(12) United States Patent
Shemer et al.

(10) Patent No.: US 8,825,152 B2
(45) Date of Patent: *Sep. 2, 2014

(54) MODULATION OF INTRACELLULAR CALCIUM CONCENTRATION USING NON-EXCITATORY ELECTRICAL SIGNALS APPLIED TO THE TISSUE

(75) Inventors: Itzik Shemer, Haifa (IL); Bella Felzen, Haifa (IL); Nissim Darvish, Moshav Tsrufa (IL); Yuval Mika, Shmurat Zichron (IL); Walid Haddad, Haifa (IL); Richardo Aviv, Haifa (IL); Yaakov Haham, Kiriat Ata (IL)

(73) Assignee: Impulse Dynamics, N.V., Curacao (AN)

( * ) Notice: Subject to any disclaimer, the term of this patent is extended or adjusted under 35 U.S.C. 154(b) by 0 days.

This patent is subject to a terminal disclaimer.

(21) Appl. No.: 10/116,201

(22) Filed: Apr. 3, 2002

(65) Prior Publication Data

US 2003/0040777 A1 Feb. 27, 2003
US 2007/0239216 A9 Oct. 11, 2007

Related U.S. Application Data

(63) Continuation of application No. PCT/IB00/01523, filed on Oct. 4, 2000, and a continuation-in-part of (Continued)

(30) Foreign Application Priority Data

Jan. 8, 1996 (IL) .......................................... 116699
Sep. 17, 1996 (IL) .......................................... 119261

(51) Int. Cl.
*A61N 1/00* (2006.01)
*A61N 1/362* (2006.01)
*A61N 1/368* (2006.01)

(52) U.S. Cl.
CPC ............. *A61N 1/3627* (2013.01); *A61N 1/3628* (2013.01); *A61N 1/368* (2013.01)
USPC .............................................................. 607/2

(58) Field of Classification Search
USPC ...................................................... 607/2, 9, 25
See application file for complete search history.

(56) References Cited

U.S. PATENT DOCUMENTS 1,918,386 A 7/1933 Esau
3,211,154 A 10/1965 Becker et al.

(Continued)

FOREIGN PATENT DOCUMENTS

EP 0156593 10/1985
EP 0220916 5/1987

(Continued)

OTHER PUBLICATIONS

R. Miledi et al. "Effects of membrane polarization on sarcoplasmic calcium release in skeletal muscle"; Proc. R. Soc. Lond. B. Biological Science, Sep. 17, 1981; 213 (1190):1-13 (abstract).*

(Continued)

*Primary Examiner* — Mark W Bockelman
(74) *Attorney, Agent, or Firm* — William H. Dippert; Eckert Seamans Cherin & Mellott, LLC

(57) ABSTRACT

According to a method and device for modulating intracellular calcium concentration in biological tissue, a stimulation probe is applied to the tissue, a non-excitatory stimulation pulse is generated, and the pulse is conveyed to the stimulation probe. In one embodiment concerning cardiac tissue, a stimulation probe is applied to a patient's heart, a signal is received from at least one sensor responsive to the patient's cardiac muscle activity, a non-excitatory stimulation pulse responsive to the signal is generated, and the pulse is conveyed to the stimulation probe.

62 Claims, 4 Drawing Sheets

Related U.S. Application Data application No. 10/039,845, filed on Oct. 23, 2001, which is a continuation of application No. 09/563,544, filed on May 1, 2000, now Pat. No. 6,363,279, which is a continuation of application No. 09/101,723, filed as application No. PCT/IL97/00012 on Jan. 8, 1997, now Pat. No. 6,317,631.

(60) Provisional application No. 60/009,769, filed on Jan. 11, 1996, provisional application No. 60/011,117, filed on Feb. 5, 1996, provisional application No. 60/026,392, filed on Sep. 16, 1996, provisional application No. 60/157,511, filed on Oct. 4, 1999.

(56) References Cited

U.S. PATENT DOCUMENTS

| | | | |
|---|---|---|---|
| 3,541,390 | A | 11/1970 | Jahnks |
| 3,572,345 | A | 3/1971 | Auphan |
| 3,587,567 | A | 6/1971 | Schiff |
| 3,651,805 | A | 3/1972 | Breiling |
| 3,651,806 | A | 3/1972 | Hirshberg |
| 3,796,221 | A | 3/1974 | Hagfors |
| 3,911,930 | A | 10/1975 | Hagfors et al. |
| 3,924,641 | A | 12/1975 | Weiss |
| 3,933,147 | A | 1/1976 | Du Vall et al. |
| 3,942,536 | A | 3/1976 | Mirowski et al. |
| 3,944,740 | A | 3/1976 | Murase et al. |
| 3,952,750 | A | 4/1976 | Mirowski et al. |
| 4,030,509 | A | 6/1977 | Heilman et al. |
| 4,055,190 | A | 10/1977 | Tany |
| 4,106,494 | A | 8/1978 | McEachern |
| 4,164,216 | A | 8/1979 | Person |
| 4,168,711 | A | 9/1979 | Cannon, III et al. |
| 4,184,493 | A | 1/1980 | Langer et al. |
| 4,202,340 | A | 5/1980 | Langer et al. |
| 4,223,678 | A | 9/1980 | Langer et al. |
| 4,237,895 | A | 12/1980 | Johnson |
| 4,273,114 | A | 6/1981 | Barkalow et al. |
| 4,293,734 | A | 10/1981 | Pepper, Jr. |
| 4,312,354 | A | 1/1982 | Walters |
| 4,315,503 | A | 2/1982 | Ryaby et al. |
| 4,316,472 | A | 2/1982 | Mirowski et al. |
| 4,337,776 | A | 7/1982 | Daly et al. |
| 4,369,791 | A | 1/1983 | Friedman |
| 4,384,585 | A | 5/1983 | Zipes |
| 4,387,717 | A | 6/1983 | Brownlee et al. |
| 4,403,614 | A | 9/1983 | Engle et al. |
| 4,406,288 | A | 9/1983 | Horwinski et al. |
| 4,407,288 | A | 10/1983 | Langer et al. |
| 4,411,268 | A | 10/1983 | Cox |
| 4,428,366 | A | 1/1984 | Findl et al. |
| 4,440,172 | A | 4/1984 | Langer |
| 4,506,680 | A | 3/1985 | Stokes |
| 4,537,195 | A | 8/1985 | McDonnell |
| 4,537,203 | A | 8/1985 | Machida |
| 4,543,738 | A | 10/1985 | Mower |
| 4,543,956 | A | 10/1985 | Herscovici |
| 4,550,221 | A | 10/1985 | Mabusth |
| 4,554,922 | A | 11/1985 | Prystowsky et al. |
| 4,554,992 | A | 11/1985 | Kassai |
| 4,559,946 | A | 12/1985 | Mower |
| 4,559,947 | A | 12/1985 | Renger et al. |
| 4,566,456 | A | 1/1986 | Koning et al. |
| 4,572,191 | A | 2/1986 | Mirowski et al. |
| 4,628,934 | A | 12/1986 | Pohndorf et al. |
| 4,637,397 | A | 1/1987 | Jones et al. |
| 4,639,720 | A | 1/1987 | Rympalski et al. |
| 4,651,716 | A | 3/1987 | Forester et al. |
| 4,674,508 | A | 6/1987 | DeCote |
| 4,679,572 | A | 7/1987 | Baker, Jr. |
| 4,686,332 | A | 8/1987 | Greanias et al. |
| 4,690,155 | A | 9/1987 | Hess |
| 4,693,253 | A | 9/1987 | Adams |
| 4,708,145 | A | 11/1987 | Tacker et al. |
| 4,717,581 | A | 1/1988 | Robblee |
| 4,726,279 | A | 2/1988 | Kepler et al. |
| 4,726,379 | A | 2/1988 | Altman et al. |
| 4,765,341 | A | 8/1988 | Mower et al. |
| 4,807,632 | A | 2/1989 | Liess et al. |
| 4,830,006 | A | 5/1989 | Haluska et al. |
| 4,834,100 | A | 5/1989 | Charms |
| 4,850,959 | A | 7/1989 | Findl |
| 4,870,974 | A | 10/1989 | Wang |
| 4,878,553 | A | 11/1989 | Yamanami et al. |
| 4,884,576 | A | 12/1989 | Alt |
| 4,914,624 | A | 4/1990 | Dunthorn et al. |
| 4,928,688 | A | 5/1990 | Mower |
| 4,967,749 | A | 11/1990 | Cohen |
| 4,971,058 | A | 11/1990 | Pless et al. |
| 4,979,507 | A | 12/1990 | Heinz et al. |
| 4,988,837 | A | 1/1991 | Murakami et al. |
| 4,996,984 | A | 3/1991 | Sweeney |
| 4,998,531 | A | 3/1991 | Bocchi et al. |
| 4,998,532 | A | 3/1991 | Griffith |
| 5,002,052 | A | 3/1991 | Haluska et al. |
| 5,003,976 | A | 4/1991 | Alt |
| 5,018,522 | A | 5/1991 | Mehra |
| 5,020,544 | A | 6/1991 | Dahl et al. |
| 5,022,396 | A | 6/1991 | Watanabe |
| 5,026,397 | A | 6/1991 | Aoki et al. |
| 5,031,617 | A | 7/1991 | Klettner |
| 5,041,107 | A | 8/1991 | Heil |
| 5,044,375 | A | 9/1991 | Bach, Jr. et al. |
| 5,048,522 | A | 9/1991 | Petrofsky |
| 5,050,612 | A | 9/1991 | Matsumura |
| 5,063,929 | A | 11/1991 | Bartelt et al. |
| 5,067,940 | A | 11/1991 | Liboff et al. |
| 5,083,564 | A | 1/1992 | Scherlag |
| 5,085,218 | A | 2/1992 | Heil et al. |
| 5,087,243 | A | 2/1992 | Avitall |
| 5,097,832 | A | 3/1992 | Buchanan |
| 5,097,833 | A | 3/1992 | Campos |
| 5,097,843 | A | 3/1992 | Soukup et al. |
| 5,101,814 | A | 4/1992 | Palti |
| 5,107,834 | A | 4/1992 | Ideker et al. |
| 5,111,814 | A | 5/1992 | Goldfarb |
| 5,111,815 | A | 5/1992 | Mower |
| 5,129,394 | A | 7/1992 | Mehra |
| 5,133,354 | A | 7/1992 | Kallok |
| 5,137,021 | A | 8/1992 | Wayne et al. |
| 5,144,554 | A | 9/1992 | Zhang et al. |
| 5,154,501 | A | 10/1992 | Svenson et al. |
| 5,156,147 | A | 10/1992 | Warren et al. |
| 5,156,149 | A | 10/1992 | Hudrlik |
| 5,161,527 | A | 11/1992 | Nappholz et al. |
| 5,163,427 | A | 11/1992 | Keimel |
| 5,163,428 | A | 11/1992 | Pless |
| 5,172,690 | A | 12/1992 | Nappholz et al. |
| 5,172,699 | A | 12/1992 | Svenson et al. |
| 5,174,286 | A | 12/1992 | Chirife |
| 5,184,616 | A | 2/1993 | Weiss |
| 5,184,620 | A | 2/1993 | Cudahy et al. |
| 5,185,620 | A | 2/1993 | Cooper |
| 5,188,104 | A | 2/1993 | Wernicke et al. |
| 5,188,106 | A | 2/1993 | Nappholz et al. |
| 5,190,036 | A | 3/1993 | Linder |
| 5,190,041 | A | 3/1993 | Palti |
| 5,190,141 | A | 3/1993 | Boldrini et al. |
| 5,199,428 | A | 4/1993 | Obel et al. |
| 5,205,284 | A | 4/1993 | Freeman |
| 5,213,098 | A | 5/1993 | Bennett et al. |
| 5,231,381 | A | 7/1993 | Duwaer |
| 5,231,988 | A | 8/1993 | Wernicke et al. |
| 5,233,985 | A | 8/1993 | Hudrlik |
| 5,236,413 | A | 8/1993 | Feiring |
| 5,243,980 | A | 9/1993 | Mehra et al. |
| 5,267,560 | A | 12/1993 | Cohen |
| 5,281,219 | A | 1/1994 | Kallok |
| 5,282,785 | A | 2/1994 | Shapland et al. |
| 5,284,491 | A | 2/1994 | Sutton et al. |
| 5,286,254 | A | 2/1994 | Shapland et al. |
| 5,292,344 | A | 3/1994 | Douglas |
| 5,305,745 | A | 4/1994 | Zacouto |

(56) References Cited

U.S. PATENT DOCUMENTS

| | | |
|---|---|---|
| 5,318,591 A | 6/1994 | Causey, III et al. |
| 5,320,543 A | 6/1994 | Barton |
| 5,320,642 A | 6/1994 | Scherlag et al. |
| 5,320,643 A | 6/1994 | Roline et al. |
| 5,324,327 A | 6/1994 | Cohen |
| 5,325,856 A | 7/1994 | Nitzsche et al. |
| 5,327,887 A | 7/1994 | Nowakowski |
| 5,346,506 A | 9/1994 | Mower et al. |
| 5,350,403 A | 9/1994 | Stroetmann et al. |
| 5,353,800 A | 10/1994 | Pohndorf et al. |
| 5,365,461 A | 11/1994 | Stein et al. |
| 5,366,485 A | 11/1994 | Kroll et al. |
| 5,366,486 A | 11/1994 | Zipes et al. |
| 5,368,040 A | 11/1994 | Carney |
| 5,370,665 A | 12/1994 | Hudrlik |
| 5,374,787 A | 12/1994 | Miller et al. |
| 5,381,160 A | 1/1995 | Landmeier |
| 5,386,835 A | 2/1995 | Elphick et al. |
| 5,386,837 A | 2/1995 | Sterzer |
| 5,387,419 A | 2/1995 | Levy et al. |
| 5,391,192 A | 2/1995 | Lu et al. |
| 5,391,199 A | 2/1995 | Ben-Haim |
| 5,397,344 A | 3/1995 | Garfield et al. |
| 5,398,683 A | 3/1995 | Edwards et al. |
| 5,402,151 A | 3/1995 | Duwaer |
| 5,411,531 A | 5/1995 | Hill et al. |
| 5,415,629 A | 5/1995 | Henley |
| 5,417,717 A | 5/1995 | Salo et al. |
| 5,419,763 A | 5/1995 | Hildebrand |
| 5,423,872 A | 6/1995 | Cigaina |
| 5,425,363 A | 6/1995 | Wang |
| 5,431,682 A | 7/1995 | Hedberg |
| 5,431,688 A | 7/1995 | Freeman |
| 5,431,693 A | 7/1995 | Schroeppel |
| 5,433,730 A | 7/1995 | Alt |
| 5,443,485 A | 8/1995 | Housworth et al. |
| 5,443,489 A | 8/1995 | Ben-Haim |
| 5,445,609 A | 8/1995 | Lattin et al. |
| 5,447,520 A | 9/1995 | Spano et al. |
| 5,447,525 A | 9/1995 | Powell et al. |
| 5,447,526 A | 9/1995 | Karsdon |
| 5,458,568 A | 10/1995 | Racchini et al. |
| 5,464,020 A | 11/1995 | Lerner |
| 5,464,429 A | 11/1995 | Hedberg et al. |
| 5,468,254 A | 11/1995 | Hahn et al. |
| 5,472,453 A | 12/1995 | Alt |
| 5,476,484 A | 12/1995 | Hedberg |
| 5,476,485 A | 12/1995 | Weinberg et al. |
| 5,476,487 A | 12/1995 | Sholder |
| 5,476,497 A | 12/1995 | Mower et al. |
| 5,482,052 A | 1/1996 | Lerner |
| 5,489,293 A | 2/1996 | Pless et al. |
| 5,495,077 A | 2/1996 | Miller et al. |
| 5,499,971 A | 3/1996 | Shapland et al. |
| 5,501,662 A | 3/1996 | Hofmann |
| 5,505,700 A | 4/1996 | Leone et al. |
| 5,510,813 A | 4/1996 | Makinwa et al. |
| 5,514,162 A | 5/1996 | Bornzin et al. |
| 5,520,642 A | 5/1996 | Bigagli et al. |
| 5,522,853 A | 6/1996 | Kroll |
| 5,527,345 A | 6/1996 | Infinger |
| 5,528,002 A | 6/1996 | Katabami |
| 5,531,764 A | 7/1996 | Adams et al. |
| 5,534,015 A | 7/1996 | Kroll et al. |
| 5,540,722 A | 7/1996 | Clare et al. |
| 5,540,730 A | 7/1996 | Terry et al. |
| 5,540,734 A | 7/1996 | Zabara |
| 5,543,588 A | 8/1996 | Bisset et al. |
| 5,543,589 A | 8/1996 | Buchana et al. |
| 5,549,646 A | 8/1996 | Katz et al. |
| 5,556,421 A | 9/1996 | Prutchi et al. |
| 5,556,760 A | 9/1996 | Nakamura et al. |
| 5,558,640 A | 9/1996 | Pfeiler et al. |
| 5,561,165 A | 10/1996 | Lautt et al. |
| 5,562,708 A | 10/1996 | Combs et al. |
| 5,565,632 A | 10/1996 | Ogawa |
| 5,568,809 A | 10/1996 | Ben-Haim |
| 5,571,143 A | 11/1996 | Hoegnelid et al. |
| 5,571,997 A | 11/1996 | Gray et al. |
| 5,578,061 A | 11/1996 | Stroetmann et al. |
| 5,584,803 A | 12/1996 | Stevens et al. |
| 5,584,804 A | 12/1996 | Klatz et al. |
| 5,584,868 A | 12/1996 | Salo et al. |
| 5,587,200 A | 12/1996 | Lorenz et al. |
| 5,589,856 A | 12/1996 | Stein et al. |
| 5,601,609 A | 2/1997 | Duncan |
| 5,601,611 A | 2/1997 | Fayram et al. |
| 5,620,468 A | 4/1997 | Mongeon et al. |
| 5,622,687 A | 4/1997 | Krishnan et al. |
| 5,626,622 A | 5/1997 | Cooper |
| 5,632,267 A | 5/1997 | Hognelid et al. |
| 5,634,895 A | 6/1997 | Igo et al. |
| 5,634,899 A | 6/1997 | Shapland et al. |
| 5,649,966 A | 7/1997 | Noren et al. |
| 5,651,378 A | 7/1997 | Matheny et al. |
| 5,654,030 A | 8/1997 | Munshi et al. |
| 5,662,687 A | 9/1997 | Hedberg et al. |
| 5,670,755 A | 9/1997 | Kwon |
| 5,674,251 A | 10/1997 | Combs et al. |
| 5,674,259 A | 10/1997 | Gray |
| 5,683,429 A | 11/1997 | Mehra |
| 5,683,431 A | 11/1997 | Wang |
| 5,687,734 A | 11/1997 | Dempsey et al. |
| 5,690,691 A | 11/1997 | Chen et al. |
| 5,697,953 A | 12/1997 | Kroll et al. |
| 5,713,924 A | 2/1998 | Min et al. |
| 5,713,929 A | 2/1998 | Hess et al. |
| 5,713,935 A | 2/1998 | Prutchi et al. |
| 5,720,768 A | 2/1998 | Verboven-Nelissen |
| 5,735,876 A | 4/1998 | Kroll et al. |
| 5,738,096 A | 4/1998 | Ben-Haim |
| 5,738,105 A | 4/1998 | Kroll |
| 5,741,211 A | 4/1998 | Renirie et al. |
| 5,741,791 A | 4/1998 | Olsen |
| 5,749,906 A | 5/1998 | Kieval et al. |
| 5,755,740 A | 5/1998 | Nappholz |
| 5,777,607 A | 7/1998 | Koolen |
| 5,779,661 A | 7/1998 | Stephen et al. |
| 5,782,876 A | 7/1998 | Flammang |
| 5,782,881 A | 7/1998 | Lu et al. |
| 5,783,951 A | 7/1998 | Inoue et al. |
| 5,790,106 A | 8/1998 | Hirano et al. |
| 5,790,107 A | 8/1998 | Kasser et al. |
| 5,792,189 A | 8/1998 | Gray et al. |
| 5,792,198 A | 8/1998 | Nappholz |
| 5,792,208 A | 8/1998 | Gray |
| 5,797,967 A | 8/1998 | KenKnight |
| 5,800,464 A | 9/1998 | Kieval |
| 5,807,234 A | 9/1998 | Bui et al. |
| 5,807,306 A | 9/1998 | Shapland et al. |
| 5,814,079 A | 9/1998 | Kieval |
| 5,824,016 A | 10/1998 | Ekwall |
| 5,825,352 A | 10/1998 | Bisset et al. |
| 5,841,078 A | 11/1998 | Miller et al. |
| 5,844,506 A | 12/1998 | Binstead |
| 5,854,881 A | 12/1998 | Yoshida et al. |
| 5,861,014 A | 1/1999 | Familoni |
| 5,861,583 A | 1/1999 | Schediwy et al. |
| 5,865,787 A | 2/1999 | Shapland et al. |
| 5,871,506 A | 2/1999 | Mower |
| 5,906,607 A | 5/1999 | Taylor et al. |
| 5,911,223 A | 6/1999 | Weaver et al. |
| 5,913,876 A | 6/1999 | Taylor et al. |
| 5,914,465 A | 6/1999 | Allen et al. |
| 5,919,216 A | 7/1999 | Houben et al. |
| 5,920,309 A | 7/1999 | Bisset et al. |
| 5,927,284 A | 7/1999 | Borst et al. |
| 5,954,761 A | 9/1999 | Machek et al. |
| 5,956,020 A | 9/1999 | D—Amico et al. |
| 5,962,246 A | 10/1999 | Ladner et al. |
| 5,991,649 A | 11/1999 | Garfield et al. |
| 5,995,872 A | 11/1999 | Bourgeois |
| 6,002,594 A | 12/1999 | Ledin et al. |
| 6,006,134 A | 12/1999 | Hill et al. |

(56) References Cited

U.S. PATENT DOCUMENTS

| | | |
|---|---|---|
| 6,023,640 A | 2/2000 | Ross |
| 6,026,326 A | 2/2000 | Bardy |
| 6,032,074 A | 2/2000 | Collins |
| 6,032,672 A | 3/2000 | Taylor |
| 6,037,882 A | 3/2000 | Levy |
| 6,041,252 A | 3/2000 | Walker et al. |
| 6,057,374 A | 5/2000 | Huntington et al. |
| 6,066,163 A | 5/2000 | John |
| 6,067,470 A | 5/2000 | Mower |
| 6,071,305 A | 6/2000 | Brown et al. |
| 6,075,520 A | 6/2000 | Inoue et al. |
| 6,083,249 A | 7/2000 | Familoni |
| 6,086,582 A | 7/2000 | Altman et al. |
| 6,093,167 A | 7/2000 | Houben et al. |
| 6,122,536 A | 9/2000 | Sun et al. |
| 6,128,007 A | 10/2000 | Seybold et al. |
| 6,133,906 A | 10/2000 | Geaghan |
| 6,135,978 A | 10/2000 | Houben et al. |
| 6,136,019 A | 10/2000 | Mower |
| 6,141,586 A | 10/2000 | Mower |
| 6,141,587 A | 10/2000 | Mower |
| 6,151,586 A | 11/2000 | Brown |
| 6,178,351 B1 | 1/2001 | Mower |
| 6,233,484 B1 | 5/2001 | Ben-Haim et al. |
| 6,233,487 B1 | 5/2001 | Mika et al. |
| 6,236,887 B1 | 5/2001 | Ben-Haim et al. |
| 6,239,389 B1 | 5/2001 | Allen et al. |
| 6,243,607 B1 | 6/2001 | Mintchev et al. |
| 6,261,280 B1 | 7/2001 | Houben et al. |
| 6,278,443 B1 | 8/2001 | Amro et al. |
| 6,285,906 B1 | 9/2001 | Ben-Haim et al. |
| 6,292,693 B1 | 9/2001 | Darvish et al. |
| 6,292,704 B1 | 9/2001 | Malonek et al. |
| 6,295,470 B1 | 9/2001 | Mower |
| 6,296,693 B1 | 10/2001 | McCarthy |
| 6,298,254 B2 | 10/2001 | Tamada |
| 6,298,268 B1 | 10/2001 | Ben-Haim et al. |
| 6,317,631 B1 * | 11/2001 | Ben-Haim et al. ............ 607/9 |
| 6,330,476 B1 | 12/2001 | Ben-Haim et al. |
| 6,337,995 B1 | 1/2002 | Mower |
| 6,341,235 B1 | 1/2002 | Mower |
| 6,343,232 B1 | 1/2002 | Mower |
| 6,363,279 B1 | 3/2002 | Ben-Haim et al. |
| 6,381,495 B1 | 4/2002 | Jenkins |
| 6,392,636 B1 | 5/2002 | Ferrari et al. |
| 6,411,847 B1 | 6/2002 | Mower |
| 6,415,178 B1 | 7/2002 | Ben-Haim et al. |
| 6,417,846 B1 | 7/2002 | Lee |
| 6,424,864 B1 | 7/2002 | Matsuura |
| 6,433,069 B1 | 8/2002 | Oeltjen et al. |
| 6,449,511 B1 | 9/2002 | Mintchev et al. |
| 6,452,514 B1 | 9/2002 | Philipp |
| 6,453,199 B1 | 9/2002 | Kobozev |
| 6,463,323 B1 | 10/2002 | Conrad-Vlasak |
| 6,463,324 B1 | 10/2002 | Ben-Haim et al. |
| 6,469,719 B1 | 10/2002 | Kino et al. |
| 6,473,069 B1 | 10/2002 | Gerpheide |
| 6,504,530 B1 | 1/2003 | Wilson et al. |
| 6,505,745 B1 | 1/2003 | Anderson |
| 6,507,093 B2 | 1/2003 | Kaneda et al. |
| 6,555,235 B1 | 4/2003 | Aufderheide et al. |
| RE38,119 E | 5/2003 | Mower |
| 6,558,345 B1 | 5/2003 | Houben et al. |
| 6,567,700 B1 | 5/2003 | Turcott et al. |
| 6,570,557 B1 | 5/2003 | Westerman et al. |
| 6,571,127 B1 | 5/2003 | Ben-Haim et al. |
| 6,572,542 B1 | 6/2003 | Houben et al. |
| 6,583,676 B2 | 6/2003 | Krah et al. |
| 6,587,093 B1 | 7/2003 | Shaw et al. |
| 6,587,721 B1 | 7/2003 | Prutchi et al. |
| 6,600,953 B2 | 7/2003 | Flesler et al. |
| 6,605,039 B2 | 8/2003 | Houben et al. |
| 6,611,258 B1 | 8/2003 | Tanaka et al. |
| 6,612,983 B1 | 9/2003 | Marschal |
| 6,630,123 B1 | 10/2003 | Woltering et al. |
| 6,633,280 B1 | 10/2003 | Matsumoto et al. |
| 6,634,895 B2 | 10/2003 | Agro et al. |
| 6,652,444 B1 | 11/2003 | Ross |
| 6,658,297 B2 | 12/2003 | Loeb |
| 6,667,740 B2 | 12/2003 | Ely et al. |
| 6,684,104 B2 | 1/2004 | Gordon et al. |
| 6,690,156 B1 | 2/2004 | Weiner et al. |
| 6,762,752 B2 | 7/2004 | Perski et al. |
| 6,781,577 B2 | 8/2004 | Shigetaka |
| 6,810,286 B2 | 10/2004 | Donovan et al. |
| 6,853,862 B1 | 2/2005 | Marchal et al. |
| 6,875,605 B1 | 4/2005 | Ma |
| 6,919,205 B2 | 7/2005 | Brighton |
| 6,949,081 B1 | 9/2005 | Chance |
| 7,006,871 B1 | 2/2006 | Darvish et al. |
| 7,027,863 B1 | 4/2006 | Prutchi et al. |
| 7,062,318 B2 | 6/2006 | Ben-Haim et al. |
| 7,076,306 B2 | 7/2006 | Marchal et al. |
| 7,092,753 B2 | 8/2006 | Darvish et al. |
| 7,167,748 B2 | 1/2007 | Ben-Haim et al. |
| 7,171,263 B2 | 1/2007 | Darvish et al. |
| 7,190,997 B1 | 3/2007 | Darvish et al. |
| 7,440,806 B1 | 10/2008 | Whitehurst et al. |
| 7,460,907 B1 | 12/2008 | Darvish et al. |
| 7,840,262 B2 | 11/2010 | Mika et al. |
| 2002/0010492 A1 | 1/2002 | Donovan et al. |
| 2002/0026141 A1 | 2/2002 | Houben et al. |
| 2002/0052632 A1 | 5/2002 | Ben-Haim et al. |
| 2002/0081732 A1 | 6/2002 | Bowlin et al. |
| 2002/0123771 A1 | 9/2002 | Ideker et al. |
| 2002/0161414 A1 | 10/2002 | Flesler et al. |
| 2002/0183682 A1 | 12/2002 | Darvish et al. |
| 2002/0183686 A1 | 12/2002 | Darvish et al. |
| 2003/0018367 A1 | 1/2003 | DiLorenzo |
| 2003/0028221 A1 | 2/2003 | Zhu et al. |
| 2003/0040777 A1 | 2/2003 | Shemer et al. |
| 2003/0055464 A1 | 3/2003 | Darvish et al. |
| 2003/0055465 A1 | 3/2003 | Ben-Haim et al. |
| 2003/0055466 A1 | 3/2003 | Ben-Haim et al. |
| 2003/0100889 A1 | 5/2003 | Duverger et al. |
| 2003/0167476 A1 | 9/2003 | Conklin |
| 2003/0181958 A1 | 9/2003 | Doubak |
| 2003/0188899 A1 | 10/2003 | Chao et al. |
| 2003/0208242 A1 | 11/2003 | Harel et al. |
| 2003/0211475 A1 | 11/2003 | Roberts |
| 2004/0059393 A1 | 3/2004 | Policker et al. |
| 2004/0095333 A1 | 5/2004 | Morag et al. |
| 2004/0105040 A1 | 6/2004 | Oh et al. |
| 2004/0106954 A1 | 6/2004 | Whitehurst et al. |
| 2004/0155871 A1 | 8/2004 | Perski et al. |
| 2004/0158289 A1 | 8/2004 | Girouard et al. |
| 2004/0162595 A1 | 8/2004 | Foley |
| 2004/0230273 A1 | 11/2004 | Cates et al. |
| 2004/0243190 A1 | 12/2004 | Ben-Haim et al. |
| 2004/0249421 A1 | 12/2004 | Harel et al. |
| 2005/0021101 A1 | 1/2005 | Chen et al. |
| 2005/0033396 A1 | 2/2005 | Ospyka |
| 2005/0065553 A1 | 3/2005 | Ben Ezra et al. |
| 2005/0095227 A1 | 5/2005 | Rosenzweig et al. |
| 2005/0192542 A1 | 9/2005 | Dev et al. |
| 2006/0036126 A1 | 2/2006 | Ross et al. |
| 2006/0079475 A1 | 4/2006 | Zhang et al. |
| 2006/0085045 A1 | 4/2006 | Harel et al. |
| 2006/0097991 A1 | 5/2006 | Hotelling et al. |
| 2006/0184207 A1 | 8/2006 | Darvish et al. |
| 2007/0016262 A1 | 1/2007 | Gross et al. |
| 2007/0027487 A1 | 2/2007 | Mika et al. |
| 2007/0027490 A1 | 2/2007 | Ben-Haim et al. |
| 2007/0060812 A1 | 3/2007 | Harel et al. |
| 2007/0088393 A1 | 4/2007 | Ben-Haim et al. |
| 2007/0156177 A1 | 7/2007 | Harel et al. |
| 2007/0161851 A1 | 7/2007 | Takizawa et al. |
| 2007/0171211 A1 | 7/2007 | Perski et al. |
| 2007/0239216 A9 | 10/2007 | Shemer et al. |
| 2007/0293901 A1 | 12/2007 | Rousso et al. |
| 2008/0058879 A1 | 3/2008 | Ben-Haim et al. |
| 2008/0065159 A1 | 3/2008 | Ben-Haim et al. |
| 2008/0065163 A1 | 3/2008 | Ben-Haim et al. |
| 2008/0065164 A1 | 3/2008 | Ben-Haim et al. |

(56) References Cited

U.S. PATENT DOCUMENTS

| | | | |
|---|---|---|---|
| 2008/0140142 | A1 | 6/2008 | Darvish et al. |
| 2009/0062893 | A1 | 3/2009 | Spehr et al. |
| 2009/0131993 | A1 | 5/2009 | Rousso et al. |
| 2009/0292324 | A1 | 11/2009 | Rousso et al. |
| 2010/0016923 | A1 | 1/2010 | Rousso et al. |
| 2010/0035963 | A1 | 2/2010 | Chajut et al. |
| 2013/0096639 | A1 | 4/2013 | Ben-Haim et al. |
| 2013/0338425 | A1 | 12/2013 | Rousso et al. |

FOREIGN PATENT DOCUMENTS

| | | |
|---|---|---|
| EP | 0250931 | 1/1988 |
| EP | 0314078 | 5/1989 |
| EP | 0481684 | 4/1992 |
| EP | 0503839 | 9/1992 |
| EP | 0528751 | 2/1993 |
| EP | 0727241 | 8/1996 |
| EP | 0910429 | 4/1999 |
| EP | 1263498 | 12/2002 |
| GB | 1394171 | 5/1975 |
| GB | 2280377 | 2/1995 |
| JP | 62-112530 | 5/1987 |
| JP | 62-275471 | 11/1987 |
| JP | 04-117967 | 4/1992 |
| JP | 04-282168 | 10/1992 |
| JP | 04-365493 | 12/1992 |
| JP | 06-169998 | 6/1994 |
| JP | 06-506619 | 7/1994 |
| JP | 07-503865 | 4/1995 |
| JP | 07-126600 | 5/1995 |
| JP | 07-144024 | 6/1995 |
| JP | 08-243176 | 9/1996 |
| RU | 2014844 | 6/1994 |
| RU | 2055606 | 3/1996 |
| RU | 2075980 | 3/1997 |
| RU | 2077273 | 4/1997 |
| RU | 2078547 | 5/1997 |
| WO | WO 91/19534 | 12/1991 |
| WO | WO 92/00716 | 1/1992 |
| WO | WO 92/13592 | 8/1992 |
| WO | WO 93/02743 | 2/1993 |
| WO | WO 93/02745 | 2/1993 |
| WO | WO 93/08874 | 5/1993 |
| WO | WO 93/18820 | 9/1993 |
| WO | WO 94/17855 | 8/1994 |
| WO | WO 95/02995 | 2/1995 |
| WO | WO 95/08316 | 3/1995 |
| WO | WO 96/10358 | 4/1996 |
| WO | WO 96/16696 | 6/1996 |
| WO | WO 97/06849 | 2/1997 |
| WO | WO 97/15227 | 5/1997 |
| WO | 97/25098 * | 7/1997 |
| WO | WO 97/24981 | 7/1997 |
| WO | WO 97/25098 | 7/1997 |
| WO | WO 97/25101 | 7/1997 |
| WO | WO 97/29679 | 8/1997 |
| WO | WO 98/10828 | 3/1998 |
| WO | WO 98/10829 | 3/1998 |
| WO | WO 98/10830 | 3/1998 |
| WO | WO 98/10831 | 3/1998 |
| WO | WO 98/10832 | 3/1998 |
| WO | WO 98/19719 | 5/1998 |
| WO | WO 99/03533 | 1/1999 |
| WO | WO 99/06105 | 2/1999 |
| WO | WO 99/09971 | 3/1999 |
| WO | WO 00/01443 | 1/2000 |
| WO | WO 00/04947 | 2/2000 |
| WO | WO 00/12525 | 3/2000 |
| WO | WO 00/16741 | 3/2000 |
| WO | WO 00/27475 | 5/2000 |
| WO | WO 00/42914 | 7/2000 |
| WO | WO 00/53257 | 9/2000 |
| WO | WO 00/74773 | 12/2000 |
| WO | WO 01/24871 | 4/2001 |
| WO | WO 01/49367 | 7/2001 |
| WO | WO 01/52931 | 7/2001 |
| WO | WO 01/66183 | 9/2001 |
| WO | WO 01/91854 | 12/2001 |
| WO | WO 01/93950 | 12/2001 |
| WO | WO 01/93951 | 12/2001 |
| WO | WO 02/10791 | 2/2002 |
| WO | WO 02/053093 | 7/2002 |
| WO | WO 02/082968 | 10/2002 |
| WO | WO 03/045493 | 6/2003 |
| WO | WO 2004/021858 | 3/2004 |
| WO | WO 2004/059393 | 7/2004 |
| WO | WO 2004/070396 | 8/2004 |
| WO | WO 2004/080533 | 9/2004 |
| WO | WO 2005/023081 | 3/2005 |
| WO | WO 2005/087310 | 9/2005 |
| WO | WO 2005/114369 | 12/2005 |
| WO | WO 2006/073671 | 7/2006 |
| WO | WO 2006/087717 | 8/2006 |
| WO | WO 2006/097934 | 9/2006 |
| WO | WO 2006/097935 | 9/2006 |
| WO | WO 2006/119467 | 11/2006 |
| WO | WO 2007/091255 | 8/2007 |

OTHER PUBLICATIONS

"The Latest Tetralogy of Fallot Discussion with Graphical Support Including Video of Echocardiography and Catherization", Pediatric Electrophysiologyicu Book ("An On-Line Resource for Pediatric Critical Care").
Adeghate et al., "Effect of Electrical Field Stimulation on Insulin and Glucagon Secretion from the Pancreas of Normal and Diabetic Rats", Hormone and Metabolic Research, 33, abst. only.
Antman et al. "Treatment of 150 Cases of Life-Threatening Digitals Intoxication with Digoxin-Specific Fab Antibody Fragments", Circulation, 81(6): 1744-1752, 1990.
Antoni et al. "Polarization Effects of Sinusoidal 50-Cycle Alternating Current on Membrane Potential of Mammalian Cardiac Fibres", Pflügers Archiv European Journal of Physiology, 314(4): 274-291, 1970.
Bach "Tach Arrhythmia Detection, Implantable Cardloverter Defibrilator Therapy: The Engineering—Clinical Interface", Kluwer Academic Publishers, (15): 303-323, 1997.
Bakker et al. "Beneficial Effects of Biventricular Pacing of Congestive Heart Failure", Pace, 17(Part II): 318, 1994.
Bakker et al. "Biventricular Pacing Improves Functional Capacity in Patients with End-Stage Congestive Heart Failure", Pace, 17(11/Part II/120): 825, 1995.
Bargheer et al. "Prolongation of Monophastic Action Potential Duration and the Refractory Period in the Human Heart by Tedisamil, A New Potassium-Blocking Agent", The European Society of Cardiology, 15(10): 1409-1414, 1994.
Bergsten et al. "Synchronous Oscillations of Cytoplasmic Ca2+ and Insulin Release in Glucose-Stimulated Pancreatic Islets", The Journal of Biological Chemistry, 269(12): 8749-8753, 1994.
Borst et al. "Coronary Artery Bypass Grating Without Cardiopulmonary Bypass and without Interuption of Native Coronary Flow Using a Novel Anastomosis Site Restraining Device (Octupus)", Journal of the American Colleges of Cardiology, 27(6): 1356-1364, 1996.
Bouaziz et al. "Direct Electrical Stimulation of Insulin Secretion by Intact Murine Islets of Langerbans Through the Culture Support", Electro-and Magnetobiology, 17(2), 1998, abst. only.
Bronzino "Biomedical Engineering Handbook", IEEE Press/CRC Press, 5(Chap.82): 1288, 1995.
Brumwell et al. "The Amplifier Sensing the Depolarization Implantable Cardioverter Dafibrillator Therapy: The Engineering-Clinical Interface", Kluwer Academic Publishers, Chap.14: 275-302, 1997.
Burfeind et al. "The Effects of Mechanical Cardiac Stabilization on Left Ventricular Performance", European Journal of Cardio-Thoracic Surgery,14: 285-289, 1998.
Cano et al. "Dose-Dependent Reversal of Dixogin-Inhibited Activity of An In-Vitro Na+K+ATPase Model by Digoxin-Specific Antibody", Toxicology Letters, 85(2): 107-1011, 1996.

(56) References Cited

OTHER PUBLICATIONS

Cazeau et al. "Multisite Pacing for End-Stage Heart Failure: Early Experience", PACE, 19(Part II): 1748-1757, 1996.
Cheng et al. "Calcium Sparks: Elementary Events Underlying Excitation-Contraction Coupling in Heart Muscle", Science, 262: 740-744, 1993.
Cooper "Postextrasystolic Potentiation: Do We Really Know What it Means and How to Use it?", Ciculation , 88(6): 2962-2971, 1993.
Coulton et al. "Magnetic Fields and Intracellular Calcium: Effects on Lymphocytes Exposed to Conditions for 'Cyclotron Resonance'", Physics in Medicine and Biology, 38, 1993. abst. only.
Davis et al. "Insulin, Oral Hypoglycemic Agents and the Pharmacology of the Endocrine Pancreas", The Pharmacological Basis of Therapeutics, Chap.60: 1487-1499, 1507-1510.
Devedeux et al. "Uterine Electromyography: A Critical Review", American Journal of Obstetrics and Gynecology, 169(6): 1636-53, 1993, pp. 1653 missing.
Dillion "Optical Recoding in the Rabbit Heart Show that Defibrillation Strenght Shocks Prolong the Duration of Depolarization and the Refractory Period", Circulation Research, 69: 842-856, 1991.
Dillon "Synchronized Repolarization After Defibrillation Shocks. A Possible Component of the Defibrillation Process Demonstration by Optical Recordings in Rabbit Heart", Circulation, 85(5): 1865-1878, 1992.
Erol-Yilmaz et al. "Reversed Remodelling of Dilated Left Sided Cardiomyopathy After Upgrading From VVIR to VVIR Biventricular Pacing", Europace, 4: 445-449, 2002.
Gill et al. "Refractory Period Extension During Ventricular Pacing at Fibrillatory Pacing Rates", PACE, 20(Part 1): 647-653, 1997.
Gilmour Jr. et al. "Dynamics of Circus Movement Re-Entry Across Canine Purkinje Fibre-Muscle Junctions", The Journal of Physiology, 476(3): 473-485, 1994.
Gilmour Jr. et al. "Overdrive Suppression of Conduction at the Canine Purkinje-Muscle Junction", Circulation, 76(6): 1388-1396, 1987.
Gold et al. "Evidence that Glucose "Marks" β Cells Resulting in Preferential Release of Newly Synthesized Insulin", Science, 218, 1982, abst. only.
Gomis et al. "Oscillatory Patterns of Electrical Activity in Mouse Pancreatic Islets of Langerhans Recorded in Vivo", Pflügers Archiv—European Journal of Physiology, 432(3): 510-515, 1996.
Gussoni et al. "Dystrophin Expression in the MDX Mouse Restored by Stem Cell Transplantation", Nature, 401(6751): 390-394, 1999.
Harn et al. "Classification of Cardiac Arrhythmias Using Fuzzy Artmap", IEEE Transactions on Biomedical Engineering, 43(4): 425-429, 1996, Astract.
Hardage et al. "Anti-Tachycardla Pacing and Cardioversion", Kluwer Academic Publishers, (6): 325-342, 1997.
Hinke et al. "Dipeptidyl Peptidase IV (DPIV/CD26) Degradation of Glucagon, Characterization of Glucagon Degradation Products adn DPIV-Resistant analogs", The Journal of Biological Chemistry, 275(6):3827-3834, 2000.
Hoffman et al. "Effects of Postextrasystolic Potentiation on Normal and Failing Hearts", Bulletin of the New York Academy of Medicine, 41(5): 498-534, 1965.
Holst et al. "Nervous Control of Pancreatic Endocrine Secretion in Pigs. I. Insulin and Glucagon Responses to Electrical Stimulation of the Vagus Nerves", Acta Physiologica, 111(1), 1981. Abstract, p. 5, r-h Col., Last Line—P.6, 1-h Col., First Line, astract only.
Horner et al. "Electrode for Recording Direction of Activation, Conduction Velocity, and Monophasic Action Potential of Myocardium", American Journal of Physiology, 272: H1917-H1927, 1997.
Jaremko et al. "Advances Toward the Implantable Artificial Pancreas for Treatment in Diabetes", Diabetes Care, 21(3):444-450, 1998.
Josephson "Clinical Cardiac Electrophysiology: Techniques and Interpertations Third Edition", Cardiology Book from C.H.I.P.S., only front page.
King et al. "The Inotropic Action of Paired Pulse Stimulation in the Normal and Falling Heart: An Experimental Study", Cardiovascular Research, 2: 122-129, 1968.

Kinslet et al. "Effect of Field Stimulation on Cellular Repolarization in Rabbit Myocardium Implications for Reentry Induction", Circulation Research, 70: 707-715, 1991.
Koller et al. "Relation Between Repolarization and Refractoriness During Programmed Electrical Stimulation in the Human Right Ventricle", Circulation, 91: 2378-2384, 1995.
Kurose et al. "Glucagon, Insulin and Somatostatin Secretion in Response to Sympathetic Neural Activation in Streptozotocin-Induced Diabetic Rats. A Study with the Isolated Perfused Rat Pancreas in Vitro", Diabetologia, 35:1035-1041, 1992.
Lindström et al. "Intracellular Calcium Oscillations in A T-Cell Line After Exposure to Extremely-Low-Frequency Magnetic Fields with Variable Frequencies and Flux Densities", Bioelectromagnetics, 16, 1995, abst. only.
Liu et al. "2-Pyridylthioureas: Novel Nonpeptides Somatostatin Agonists with SST4 Selectivity", Current Pharmaceutical Design, 5(4):255-263, 1999.
Loginov "Accumulation of Calcium Ions in Myocardial Sarcoplasmic Reticulum of Restrained Rats Exposed to the Pulsed Electromagnetic Field", Aviakosm Ekolog Med, 26(2), 1992, abst. only.
Loginov et al. "Effects of an Impulse Electromagnetic Field on Calcium Ion Accumulation in the Sarcoplasmic Reticulum of the Rat Myocardium", Kosm Biol Aviakosm Med, 25(5), 1991, abst. only.
Lubart et al. "Effect of Light on Calcium Transport in Bull Sperm Cells", J. Photochemical Photobiology, 15(4): 337-341, 1992.
Luiken et al. "Contraction-Induced Fatty Acid Translocase/CD36 Translocation in Rat Cardiac Myocytes is Mediated Through AMP-Activated Protein Kinase Signaling", Diabetes, 52: 1627-1634, 2003.
Magnus et al. "Model of β-Cell Mitochondrial Calcium Handling and Electrical Activity. II. Mitochondrial Variables", American Journal of Physiology, AJP—Cell Physiology, 274(43): C1174-1184, 1998.
Matheny et al. "Vagus Nerve Stimulations as a Method to Temporarily Slow or Arrest the Heart", Annals of Thoracic Surgery, 63(6): S28-29, 1997. Abstract.
McVeigh et al. "Noninvasive Measurement of Transmural Gradients in Myocardial Strain with MR Imaging", Radiology, 180(3): 677-684, 1991.
Mercando et al. "Automated Detection of Tachycardias by Antitachycardia Devices", Cardiac Electrophysiology: From Cell to Bedside, Chap.100: 943-948, 2004.
Merck "The Merck Manual", 16th Ed, Section 3, 1992, subsection 25 of section 3 only.
Meurer et al. "Properties of Native and In Vitro Glycosylated Forms of the Glucagon-Like Peptide-I Receptor Antagonist Exendin(9-39)", Metabolism, 48(6), 1999. abst. only.
Misler et al. "Electrophysiology of Stimulus-Secretion Coupling in Human b-Cells", Diabetes, 41, 1999, abst. only.
Moran et al. "Digoxin-Specific Fab Fragments Impair Renal Function in the Rat", Journal if Pharmacy and Pharmacology, 46(10): 854-856, 1994.
Morse et al. "A Guide to Cardiac Pacemakers, Defibrillators and Related Products", Pacing and Clinical Electrophysiology, 15(4), 1992, Abstract.
Nadal et al. "Homologous and Heterologous Asynchronicity Between Identified α-, β- and δ-Cells Within Intact Islets of Langerhans in the Mouse", Journal of Physiology, 517 (Pt. 1): 85-93, 1999. Abstract.
Nannini et al. "Muscle Recruitment with Intrafascicular Electrodes", IEEE Transactions in Biomedical Engineering, 38: 769-776, 1991.
Ohinata et al. "Proadrenomedullin N-Terminal 20 Peptide (PAMP) Elevates Blood Glucose Levels Via Bombesin Receptor in Mice", FEBS Letters, 473(2), 2000, only 1 page submitted.
Palti et al. "Islets of Langerhans Generate Wavelike Electric Activity Modulated by Glucose Concentration", Diabetes, 45, 1996, only 1 page.
Park et al. "Significant Cholinergie Role in Secreted-Stimulated Exocrine Secretion in Isolated Rat Pancreas", American Journal of Physiology, 274(2):413-418, 1998.
Patterson et al. "Therapeutic Angiogenesis—The New Electrophysiology?", Circulation, 99(20): 2614-2616, 1999.
Paul et al. "Automatic Recognition of Ventricular Arrhythmias Using Temporal Electrogram Analysis", PACE, 14: 1265-1273, 1991.

(56) References Cited

OTHER PUBLICATIONS

Pokrovsky et al. "Pysiology of Man", Moscow Medicine, Translation of Extracts, 1997, only p. 82-83, 82-154 provided.
Pørksen et al. "Pulsatile Insulin Secretion: Detection, Regulation and Role in Diabetes, Section 6: Pulsatile and Phasic Insulin Release in Normal and Diabetic Men",Diabetes, 51(Suppl. 1/Sec.6): S245-S254, 2002.
Ranjan et al. "Electrical Stimulation of Cardiac Myocytes", Annals of Biomedical Engineering, 23(6): 812-821, 1995. Abstract.
Rivera et al. "Regulation of Protein Secretion Through Controlled Aggregation in the Endoplasmic Reticulum",Science, 287, 2000, abst only.
Saihara "Summation of Excitation with a Single Conditioning Stimulus in the Canine Heart", PACE, 13: 52-58, 1990.
Saksena et al. "Prevention of Recurrent Atrial Fibrillation with Chronic Dual-Site Atrial Pacing", Journal of the American College of Cardiology, JACC, 28(3): 687-694, 1996. Abstract.
Sakurma et al. "A Model Analysis of Aftereffects of High-Intensity DC Stimulation on Action Potential of Ventricular Muscle", IEEE Transactions on Biomedical Engineering, 45(2): 258-267, 1998, pp. 260, 262, 264, 266 missing.
Saveliev et al. "Guidebook on Clinical Endoscopy", Moscow Medicine, p. 21, 35, 1985.
Schirra et al. "Exendin (9-39) Amide is An Antagonist of Glucagon-Like Peptide-1(7-36) Amide in Humans", Journal of Clinical Investigation, 101(7): 1421-1430, 1998.
Schirra et al. "Mechanisms if the Antidiabetic Action of Subcutaneous Glucagon-Like Peptide-1(7-36)Amide in Non-Insulin Dependent Diabetes Mellitus", Journal of Endocrinology, 156, 1998, only 1 page.
Schwartz et al. "Exposure of Frog Hearts to CW or Amplitude-Modified VHF Fields: Selective Efflux of Calcium Ions at 16 Hz", Bioelectromagnetics, 11(4): 349-358, 1990, Abstract only.
Serre et al. "Exedin-(9-39) is Au Inverse Agonist of the Murine Glucagon-Like Peptide-1 Receptor" Implacations for Basal Intracellular Cyclic Adenosine 3', 5'-Monophosphate Levels and B-Cell Glucose Competence, Endocrinology, 139(11): 4448-4454, 1998.
Shah et al. "Impact of Lack of Suppression of Glucagon on Glucose Tolerancein Humans", American Journal of Physiology, 277:E283-E290, 1999.
Shmit et al. "Physiology of Man", Moscow Mir, 1:78, Translation of Extract, 1996.
Shubs et al. "Physiology if Vessel Smooth Muscles",Kiev Naukova Dumka, 142:11-15, 1988.
Shumaik et al. "Oleander Poisoning: Treatment with Digoxin-Specific Fab Antibody Fragments", Annals of Emergency Medicine, 17(7): 732-735, 1988.
Singh et al. "Effects of Islet Hormones on Nerve-Mediated and Acetylcholine-Evokedsecretory Responses in the Isolated Pancreas of Normal and Diabetic Rats", International Journal of Molecular Medicine, 1(3), 1998, only abst.
Skale et al. "Inhibition of Premature Ventricular Extranstimuli by Subthreshold Conditioning Stimuli", Journal of the American College of Cardiology, 6(1): 133-140, 1985.
Solomonow et al. "Control of Muscle Contractile Force Through Indirect High-Frequency Stimulation", American Journal of Physical Medicine, 67(2): 71-82, 1983, Abstract.
Soria et al. "Cytosolic Calcium Oscillations and Insulin Release in Pancreatic Islets of Langerhans", Diabetes & Metabolism, 24(1): 37-40, 1998.
Stevenson et al. "Electrophysiological Characteristics of Ventricular Tachycardia of Fibrillation in Relation to Age of Myocardial infarction", Am J. Cardiol. 57(6).
Supino "The System", Implantable Cardioverter Defibrillator Therapy: The Engineering-Clinical Interface, Kluwer Academic Publishers, Chap.8: 163-172, 1997.
Sweeney et al. "Refractory Interval After Transcardiac Shocks During Ventricular Fibrillation", Circulation, 94: 2947-2952, 1996.
Sweeney et al. "Ventricular Refractory Period Extension Caused by Defibrillation Shocks", Circulation, 82: 965-972, 1990.
Sweeney et al. "Countershock Strength-Duration Relationship for Myocardial Refractory Period Extension", Academy of Emergency Medicine, 2: 57-92, 1995.
Swerdlow et al. "Cardiovascular Collapse Caused by Electrocardiographically Silent 60-Hz Intracardiac Leakage Current: Implications for Electrical Safety", Circulation, 99: 2559-2564, 1999.
Talit et al. "The Effect of External Cardiac Pacing on Stroke Volume", PACE, 13: 598-602, 1990.
Taniguchi et al. "Inhomogencity of Cellular Activation Time and VMax in Normal Myocardial Tissue Under Electrical Field Stimulation", American Journal of Physiology, 267: H694-H705, 1994, p. 694-696, 700, 702-703, unreadable.
Thakor et al. "Effect of Varying Pacing Waveform Shapes on Propagation and Hemodynamics in the Rabbit Heart", American Journal of Cardiology, 79(6A): 36-43, 1997, p. 37 missing.
Todd et al. "Subcutaneous Glucagon-Like Peptide-I Improve Postprandial Glycaemic Control Over a 3-Week Period in Patients with Early Type 2 Diabetes", Clinical Science, 95: 325-329, 1998.
Tsong "Electroporation of Cell Membranes", Biophysical Journal, 60: 297-306, 1991.
Valdeolmillos et al. "In Vitro Synchronous Membrane Potential Oscillations in Mouse Pancreatic B-Cells: Lack of Co-Ordination Between Islets", Journal of Physiology, 493(1): 9-18, 1996.
Van Ripper et al. "Electrical Field Stimulation, Mediated Relaxation of a Rabbit Middle Celebral Artery", Circulation Research, 70: 1104-1112, 1992.
Verrier et al. "Electrophysiologic Basis for T Wave Alternans as an Index of Vulnerability to Ventricular Fibrillation", Journal of Cardiovascular Electrophysiology, 5(5): 445-461, 1994, Abstract.
Wang et al. "Islet Amyloid Polypeptide Tonally Inhibits β-, α-, and Cell Secretion in Isolated Rat Pancreatic Islets", American Journal of Physiology, 276:E19-E24, 1999.
Webster Design of Cardiac Pacemakers, IEEE Press, p. xi-xiii, 1995.
Wessale et al. "Stroke Volume and the Three Phase Cardiac Output Rate Relationship with Ventricular Pacing", PACE, 13: 673-680, 1990.
Windle et al. "Subthreshold Conditioning Stimuli Prolong Human Ventricular Refractoriness", The American Journal of Cardiology, 57(6): 381-386, 1996. Abstract.
Wirtzfeld et al. "Physiological Pacing: Present Status and Future Developments", PACE, 10(Pt.I): 41-57, 1987.
Xue et al. "Neural-Network-Based Adaptive Matohed Filtering for QRS Detection", IEEE Transactions on Biomedical Engineering, 39(4): 317-329, 1992, Abstract.
Yokoyama "The Phase of Supernormal Excitation in Relation to the Strength of Subthreshold Stimuli", Japanese Heart Journal, 17(3): 315-325, 1975.
Zhou et al. "Preventions of Action Potentials During Extracellular Electrical Stimulation of Long Duration", Journal of Cardiovascular Electrophysiology, 8(7): 779-789, 1997. Abstract.
Zipes et al. "Cardiac Electrophysiology—From Cell to Bedside", Saunders Co., 4th Ed., 1990.
Examination Report Dated Jun. 26, 2009 From the Government of India, Patent Office Re.: Application No. 1161/CHENP/2006.
Office Action Dated Jul. 13, 2009 From the State Intellectual Property Office of the People's Republic of China Re.: Application No. 200480027083.3 and Its Translation Into English.
Official Action Dated Jun. 1, 2009 From the US Patent and Trademark Office Re.: U.S. Appl. No. 10/039,845.
Official Action Dated Dec. 2, 2009 From the US Patent and Trademark Office Re.: U.S. Appl. No. 11/932,149.
Official Action Dated Dec. 3, 2009 From the US Patent and Trademark Office Re.: U.S. Appl. No. 11/318,845.
Official Action Dated Sep. 3, 2009 From the US Patent and Trademark Office Re.: U.S. Appl. No. 10/804,560.
Official Action Dated Dec. 4, 2009 From the US Patent and Trademark Office Re.: U.S. Appl. No. 11/884,389.
Official Action Dated Oct. 6, 2009 From the US Patent and Trademark Office Re.: U.S. Appl. No. 11/550,560.
Official Action Dated Sep. 14, 2009 From the US Patent and Trademark Office Re.: U.S. Appl. No. 11/931,889.
Official Action Dated Aug. 18, 2009 From the US Patent and Trademark Office Re.: U.S. Appl. No. 10/570,576.

(56) References Cited

OTHER PUBLICATIONS

Official Action Dated Sep. 25, 2009 From the US Patent and Trademark Office Re.: U.S. Appl. No. 10/526,708.
Official Action Dated Aug. 28, 2009 From the US Patent and Trademark Office Re.: U.S. Appl. No. 11/802,685.
Official Action Dated Aug. 28, 2009 From the US Patent and Trademark Office Re.: U.S. Appl. No. 11/932,064.
Request for Ex Parte Reexamination of U.S. Patent No. 6,330,476—IDS Dated May 31, 2006.
Response Dated Nov. 22, 2009 to Official Action of Jun. 1, 2009 From the US Patent and Trademark Office Re.: U.S. Appl. No. 10/039,845.
Gardner "Natriuretic Peptides: Markers or Modulators of Cardiac Hypertrophy?", Trends in Endocrinology and Metabolism, 14(9): 411-416, Nov. 2003.
Official Action Dated Apr. 28, 2011 From the US Patent and Trademark Office Re. U.S. Appl. No. 11/931,889.
Official Action Dated Mar. 31, 2011 From the US Patent and Trademark Office Re. U.S. Appl. No. 11/673,812.
Response Dated Aug. 10, 2011 to Official Action of May 13, 2011 From the US Patent and Trademark Office Re. U.S. Appl. No. 11/933,168.
Response Dated Jul. 27, 2011 to Official Action of Apr. 28, 2011 From the US Patent and Trademark Office Re. U.S. Appl. No. 11/931,889.
Official Action Dated Aug. 9, 2011 From the US Patent and Trademark Office Re.: U.S. Appl. No. 11/932,149.
Pre-Appeal Brief Request for Review Dated Aug. 9, 2011 From the US Patent and Trademark Office Re. U.S. Appl. No. 11/933,168.
Response Dated Aug. 31, 2011 to Official Action of Mar. 31, 2011 From the US Patent and Trademark Office Re. U.S. Appl. No. 11/673,812.
Response Dated Aug. 24, 2010 to the Supplementary European Search Report of Jun. 7, 2010 From the European Patent Office Re. U.S. Appl. No. 04770468.9.
Notice of Allowance Dated Dec. 28, 2010 From the US Patent and Trademark Office Re.: U.S. Appl. No. 11/932,064.
Official Action Dated Jan. 13, 2011 From the US Patent and Trademark Office Re.: U.S. Appl. No. 11/931,889.
Official Action Dated Dec. 14, 2010 From the US Patent and Trademark Office Re.: U.S. Appl. No. 11/884,389.
Notice of Non-Compliant Amendment Dated Jun. 1, 2011 From the US Patent and Trademark Office Re. U.S. Appl. No. 11/886,154.
Response Dated May 15, 2011 to Office Action of Nov. 25, 2010 From the State Intellectual Property Office (SIPO) of the People's Republic of China Re.: Application No. 200480012687.5. & Claims in English.
Translation of Office Action Dated Apr. 20, 2011 From the State intellectual Property Office (SIPO) of the People's Republic of China Re.: Application No. 200480012687.5.
Official Action Dated Sep. 27, 2010 From the US Patent and Trademark Office Re.: U.S. Appl. No. 10/804,560.
Response Dated Oct. 13, 2010 to Official Action of Apr. 30, 2010 From the US Patent and Trademark Office Re.: U.S. Appl. No. 11/932,149.
U.S. Appl. No. 90/008,688, filed Jun. 15, 2007, Ben-Haim.
U.S. Appl. No. 90/008,689, Ben Haim.
U.S. Appl. No. 90/008,707, filed Jun. 7, 2007, Ben Haim.
U.S. Appl. No. 95/000,032, Ben Haim.
Amended Request for Ex Parte Reexamination of U.S. Patent No. 6,317,631 Dated Aug. 20, 2007 From the US Patent and Trademark Office Re.: U.S. Appl. No. 90/008,689.
Communication Pursuant to Article 94(3) EPC Dated Mar. 2, 2009 From the European Patent Office Re.: Application No. 05853465.2.
Communication Pursuant to Article 94(3) EPC Dated Jan. 27, 2010 From the European Patent Office Re. Application No. 07110023.4.
Communication Pursuant to Article 94(3) EPC Dated Jan. 28, 2009 From the European Patent Office Re.: Application No. 03794043.4.
Communication Pursuant to Article 94(3) EPC Dated Jan. 29, 2009 From the European Patent Office Re.: Application No. 04106247.2.
Communication Pursuant to Article 96(2) EPC Dated Mar. 2, 2007 From the European Patent Office Re.: Application No. 97929478.2.
Communication to Pursuant to Article 94(3) EPC Dated Mar. 4, 2009 From the European Search Report Re.: Application No. 06759102.4.
Inter Partes Reexamination Communication of U.S. Patent No. 6,330,476 Dated Sep. 4, 2007 From the US Patent and Trademark Office Re.: U.S. Appl. No. 95/000,032.
International Preliminary Report on Patentability Dated Dec. 1, 2004 From the International Preliminary Examining Authority Re.: Application No. PCT/IL03/00736.
International Preliminary Report on Patentability Dated Nov. 15, 2007 From the International Bureau of WIPO Re.: Application No. PCT/US2006/017281.
International Preliminary Report on Patentability Dated Jun. 21, 2007 From the International Bureau of WIPO Re.: Application No. Jun. 21, 2007.
International Preliminary Report on Patentability Dated Sep. 27, 2007 From the International Bureau of WIPO Re.: Application No. PCT/IL2006/000345.
International Preliminary Report on Patentability Dated Aug. 30, 2007 From the International Bureau of WIPO Re.: Application No. PCT/IL2006/000204.
International Search Report and the Written Opinion Dated May 12, 2006 From the International Searching Authority Re.: Application No. PCT/US05/44557.
International Search Report and the Written Opinion Dated Oct. 16, 2006 From the International Searching Authority Re.: Application No. PCT/US06/17281.
International Search Report and the Written Opinion Dated Sep. 29, 2006 From the International Searching Authority Re.: Application No. PCT/IL06/00204.
International Search Report Dated Sep. 13, 2004 From the International Searching Authority Re.: Application No. PCT/IL03/00736.
Invitation Pursuant to Rule 62a(1) EPC and Rule 63(1) EPC Dated May 5, 2010 From the European Patent Office Re.: Application No. 04719312.3.
Notice of Allowance Dated Sep. 7, 2006 From the US Patent and Trademark Office Re.: U.S. Appl. No. 10/804,560.
Notice of Allowance Dated May 27, 2010 From the US Patent and Trademark Office Re.: U.S. Appl. No. 10/549,216.
Notification of Reasons of Rejection Dated Sep. 29, 2008 From the Japanese Patent Office Re.: Application No. 2004-534013 and its Translation into English.
Office Action Dated Dec. 4, 2009 From the State Intellectual Property Office of the People's Republic of China Re.: Application No. 03824661.9 and its Translation Into English.
Office Action Dated Nov. 7, 2008 From the State Intellectual Property Office of the People's Republic of China Re.: Application No. 03824661.9 and Its Translation Into English.
Office Action Dated Jan. 8, 2010 From the State Intellectual Property Office (SIPO) of the People's Republic of China Re.: Application No. 200480012687.5 and Its Translation Into English.
Office Action Dated May 8, 2009 From the State Intellectual Property Office of the People's Republic of China Re.: Application No. 03824661.9 and Its Translation Into English.
Office Action Dated Oct. 12, 2004 From the Israeli Patent Office Re.: Application No. 128955.
Office Action Dated Dec. 15, 2008 From the State Intellectual Property Office (SIPO) of the People's Republic of China Re.: Application No. 200480012687.5 and Its Translation Into English.
Official Action Dated Aug. 1, 2007 From the US Patent and Trademark Office Re.: U.S. Appl. No. 90/008,312.
Official Action Dated Oct. 1, 2009 From the US Patent and Trademark Office Re.: U.S. Appl. No. 10/237,263.
Official Action Dated Nov. 3, 2009 From the US Patent and Trademark Office Re.: U.S. Appl. No. 11/931,724.
Official Action Dated Feb. 4, 2010 From the US Patent and Trademark Office Re.: U.S. Appl. No. 10/039,845.
Official Action Dated Jan. 5, 2010 From the US Patent and Trademark Office Re.: U.S. Appl. No. 11/802,685.
Official Action Dated May 5, 2010 From the US Patent and Trademark Office Re.: U.S. Appl. No. 11/884,389.

(56) References Cited

OTHER PUBLICATIONS

Official Action Dated Nov. 5, 2009 From the US Patent and Trademark Office Re.: U.S. Appl. No. 10/549,216.
Official Action Dated Oct. 5, 2010 From the US Patent and Trademark Office Re.: U.S. Appl. No. 10/039,845.
Official Action Dated Mar. 6, 2009 From the US Patent and Trademark Office Re.: U.S. Appl. No. 11/932,064.
Official Action Dated Aug. 8, 2007 From the US Patent and Trademark Office Re.: U.S. Appl. No. 10/804,560.
Official Action Dated Oct. 8, 2009 From the US Patent and Trademark Office Re.: U.S. Appl. No. 10/116,201.
Official Action Dated Jul. 9, 2007 From the US Patent and Trademark Office Re.: U.S. Appl. No. 10/237,263.
Official Action Dated Jun. 11, 2010 From the US Patent and Trademark Office Re.: U.S. Appl. No. 11/550,560.
Official Action Date Jun. 11, 2010 From the US Patent and Trademark Office Re.: U.S. Appl. No. 11/932,064.
Official Action Dated Sep. 11, 2008 From the US Patent and Trademark Office Re.: U.S. Appl. No. 10/237,263.
Official Action Dated Sep. 12, 2008 From the US Patent and Trademark Office Re.: U.S. Appl. No. 10/039,845.
Official Action Dated Sep. 13, 2007 From the US Patent and Trademark Office Re.: U.S. Appl. No. 10/237,263.
Official Action Dated Jul. 14, 2008 From the US Patent and Trademark Office Re.: U.S. Appl. No. 10/526,708.
Official Action Dated Jul. 15, 2008 From the US Patent and Trademark Office Re.: U.S. Appl. No. 10/116,201.
Official Action Dated Apr. 16, 2010 From the US Patent and Trademark Office Re.: U.S. Appl. No. 11/566,775.
Official Action Dated Jun. 17, 2010 From the US Patent and Trademark Office Re.: U.S. Appl. No. 10/549,216.
Official Action Dated Apr. 18, 2007 From the US Patent and Trademark Office Re.: U.S. Appl. No. 10/804,560.
Official Action Dated Jul. 18, 2007 From the US Patent and Trademark Office Re.: U.S. Appl. No. 10/039,845.
Official Action Dated Jul. 19, 2007 From the US Patent and Trademark Office Re.: U.S. Appl. No. 10/526,708.
Official Action Dated Jun. 19, 2008 From the US Patent and Trademark Office Re.: U.S. Appl. No. 10/237,263.
Official Action Dated Jan. 21, 2009 From the US Patent and Trademark Office Re.: U.S. Appl. No. 10/570,576.
Official Action Dated Jun. 23, 2009 From the US Patent and Trademark Office Re.: U.S. Appl. No. 10/549,216.
Official Action Dated Jun. 26, 2008 From the US Patent and Trademark Office Re.: U.S. Appl. No. 11/536,794.
Official Action Dated May 26, 2010 From the US Patent and Trademark Office Re.: U.S. Appl. No. 11/318,845.
Official Action Dated Apr. 27, 2010 From the US Patent and Trademark Office Re.: U.S. Appl. No. 10/570,576.
Official Action Dated Mar. 27, 2008 From the US Patent and Trademark Office Re.: U.S. Appl. No. 10/804,560.
Official Action Dated Jun. 28, 2010 From the US Patent and Trademark Office Re.: U.S. Appl. No. 11/931,889.
Official Action Dated Apr. 30, 2010 From the US Patent and Trademark Office Re.: U.S. Appl. No. 11/931,724.
Official Action Dated Apr. 30, 2010 From the US Patent and Trademark Office Re.: U.S. Appl. No. 11/932,149.
Official Action Dated Aug. 31, 2007 From the US Patent and Trademark Office Re.: U.S. Appl. No. 11/536,794.
Official Action Dated Jul. 31, 2008 From the US Patent and Trademark Office Re.: U.S. Appl. No. 11/318,845.
Official Action Dated Mar. 31, 2010 From the US Patent and Trademark Office Re.: U.S. Appl. No. 10/237,263.
Request for Ex Parte Reexamination of U.S. Patent No. 6,363,279—IDS Submitted Dec. 31, 2007 From the US Patent and Trademark Office Re.: U.S. Appl. No. 90/008,688.
Request for Ex Parte Reexamination of U.S. Patent No. 6,363,279—Notice of Intent to Issue Reexamination Certificate Dated Mar. 18, 2009 From the US Patent and Trademark Office Re.: U.S. Appl. No. 90/008,688.
Request for Ex Parte Reexamination of U.S. Patent No. 6,363,279—Official Action Dated Jun. 20, 2008 From the US Patent and Trademark Office Re.: U.S. Appl. No. 90/008,688.
Request for Ex Parte Reexamination of U.S. Patent No. 6,363,279—Order Granting Request Dated Nov. 5, 2007 From the US Patent and Trademark Office Re.: U.S. Appl. No. 90/008,688.
Request for Ex Parte Reexamination of U.S. Patent No. 6,363,279 Dated Jun. 8, 2007 From the US Patent and Trademark Office Re.: U.S. Appl. No. 90/008,688.
Request for Ex Parte Reexamination of U.S. Patent No. 6,363,279, Response to Official Action Dated Jun. 20, 2008 Submitted Aug. 20, 2008 From the US Patent and Trademark Office Re.: U.S. Appl. No. 90/008,688.
Request for Ex Parte Reexamination of U.S. Patent No. 6,236,887—IDS Submitted Oct. 17, 2007 From the US Patent and Trademark Office Re.: U.S. Appl. No. 90/008,707.
Request for Ex Parte Reexamination of U.S. Patent No. 6,236,887—Notice of Intent to Issue Ex Parte Examination Certificate Dated Mar. 19, 2009 From the US Patent and Trademark Office Re.: U.S. Appl. No. 90/008,707.
Request for Ex Parte Reexamination of U.S. Patent No. 6,236,887—Official Action and IDS Considered Dated Jun. 20, 2008 From the US Patent and Trademark Office Re.: U.S. Appl. No. 90/008,707.
Request for Ex Parte Reexamination of U.S. Patent No. 6,236,887—Official Action Granting Request for Ex Parte Examination Dated Aug. 17, 2007 From the US Patent and Trademark Office Re.: U.S. Appl. No. 90/008,707.
Request for Ex Parte Reexamination of U.S. Patent No. 6,236,887 Dated Jun. 13, 2007 From the US Patent and Trademark Office Re.: U.S. Appl. No. 90/008,707.
Request for Ex Parte Reexamination of U.S. Patent No. 6,298,268—Certificate of Reexamination Issued Mar. 7, 2006, U.S. Appl. No. 90/006,788.
Request for Ex Parte Reexamination of U.S. Patent No. 6,298,268—IDS Considered Feb. 22, 2005, U.S. Appl. No. 90/006,788.
Request for Ex Parte Reexamination of U.S. Patent No. 6,298,268—Notice of Intent to Issue Certificate of Reexamination Dated Mar. 29, 2005, U.S. Appl. No. 90/006,788.
Request for Ex Parte Reexamination of U.S. Patent No. 6,298,268 Dated Oct. 10, 2003, U.S. Appl. No. 90/006,788.
Request for Ex Parte Reexamination of U.S. Patent No. 6,298,268 Order Granting Request for Ex Parte Reexamination Dated Dec. 19, 2003, U.S. Appl. No. 90/006,788.
Request for Ex Parte Reexamination of U.S. Patent No. 6,317,631—Amendment in Response to Official Action Dated Jun. 20, 2008, filed Aug. 20, 2008 From the US Patent and Trademark Office Re.: U.S. Appl. No. 90/008,689.
Request for Ex Parte Reexamination of U.S. Patent No. 6,317,631—IDS Dated Sep. 26, 2008 From the US Patent and Trademark Office Re.: U.S. Appl. No. 90/008,689.
Request for Ex Parte Reexamination of U.S. Patent No. 6,317,631—IDS Dated Dec. 31, 2007 From the US Patent and Trademark Office Re.: U.S. Appl. No. 90/008,689.
Request for Ex Parte Reexamination of U.S. Patent No. 6,317,631—Notice of Intent to issue Certificate of Reexamination Dated Mar. 18, 2009 From the US Patent and Trademark Office Re.: U.S. Appl. No. 90/008,689.
Request for Ex Parte Reexamination of U.S. Patent No. 6,317,631—Official Action Dated Jun. 20, 2008, U.S. Appl. No. 90/008,689.
Request for Ex Parte Reexamination of U.S. Patent No. 6,317,631—Order Granting Reexamination Dated Nov. 5, 2007, U.S. Appl. No. 90/008,689.
Request for Ex Parte Reexamination of U.S. Patent No. 6,317,631—IDS Dated Jun. 8, 2007, U.S. Appl. No. 90/008,689.
Request for Ex Parte Reexamination of U.S. Patent No. 6,330,476—Comments by 3rd Party Requestor, Response Thereto and Official Action Issued Jul. 16, 2008, U.S. Appl. No. 95/000,032.
Request for Ex Parte Reexamination of U.S. Patent No. 6,330,476—Communication of Right to Appeal dated Jul. 16, 2008, U.S. Appl. No. 95/000,032.
Request for Ex Parte Reexamination of U.S. Patent No. 6,330,476—IDS Filed May 4, 2007, U.S. Appl. No. 95/000,032.

(56) References Cited

OTHER PUBLICATIONS

Request for Ex Parte Reexamination of U.S. Patent No. 6,330,476—Official Action by USPTO Issued Mar. 23, 2004, U.S. Appl. No. 95/000,032.
Request for Ex Parte Reexamination of U.S. Patent No. 6,330,476—Order Granting Request for Reexamination Dated Mar. 23, 2004 From the US Patent and Trademark Office Re.: U.S. Appl. No. 95/000,032.
Request for Ex Parte Reexamination of U.S. Patent No. 6,330,476 Dated Dec. 31, 2003 From the US Patent and Trademark Office Re.: U.S. Appl. No. 95/000,032.
Request for Ex Parte Reexamination of U.S. Patent No. 6,463,324—Amendment in Response to Official Action Dated Aug. 1, 2007, filed Oct. 1, 2007 From the US Patent and Trademark Office Re.: U.S. Appl. No. 90/008,312.
Request for Ex Parte Reexamination of U.S. Patent No. 6,463,324—Certificate of Reexamination Dated Apr. 29, 2008 From the US Patent and Trademark Office Re.: U.S. Appl. No. 90/008,312.
Request for Ex Parte Reexamination of U.S. Patent No. 6,463,324—Official Action—Notice of Intent to Reexamine Dated Jan. 24, 2008 From the US Patent and Trademark Office Re.: U.S. Appl. No. 90/008,312.
Request for Ex Parte Reexamination of U.S. Patent No. 6,463,324—Official Action Dated Aug. 1, 2007 From the US Patent and Trademark Office Re.: U.S. Appl. No. 90/008,312.
Request for Ex Parte Reexamination of U.S. Patent No. 6,463,324—Official Action, Interview Summary and References Considered Dated Nov. 6, 2007 From the US Patent and Trademark Office Re.: U.S. Appl. No. 90/008,312.
Request for Ex Parte Reexamination of U.S. Patent No. 6,463,324 Dated Nov. 1, 2006 From the US Patent and Trademark Office Re.: U.S. Appl. No. 90/008,312.
Response Dated Jul. 1, 2010 to Invitation Pursuant to Rule 62a(1) EPC and Rule 63(1) EPC of May 5, 2010 From the European Patent Office Re.: Application No. 04719312.3.
Response Dated Mar. 1, 2010 to Official Action of Aug. 28, 2009 From the US Patent and Trademark Office Re.: U.S. Appl. No. 11/932,064.
Response Dated Oct. 1, 2007 to Official Action of Aug. 1, 2007 From the US Patent and Trademark Office Re.: U.S. Appl. No. 90/008,312.
Response Dated Sep. 1, 2004 to Communication Pursuant to Article 96(2) EPC of Mar. 2, 2004 From the European Patent Office Re.: Application No. 97929478.2.
Response Dated Feb. 2, 2010 to Official Action of Dec. 2, 2009 From the US Patent and Trademark Office Re.: U.S. Appl. No. 11/932,149.
Response Dated Apr. 3, 2008 to Official Action of Jan. 3, 2008 From the US Patent and Trademark Office Re.: U.S. Appl. No. 10/116,201.
Response Dated Mar. 3, 2010 to Official Action of Sep. 3, 2009 From the US Patent and Trademark Office Re.: U.S. Appl. No. 10/804,560.
Response Dated May 3, 2010 to Official Action of Dec. 3, 2009 From the US Patent and Trademark Office Re.: U.S. Appl. No. 11/318,845.
Response Dated Feb. 4, 2010 to Official Action of Dec. 4, 2009 From the US Patent and Trademark Office Re.: U.S. Appl. No. 11/884,389.
Response Dated Mar. 4, 2010 to Official Action of Nov. 5, 2010 From the US Patent and Trademark Office Re.: U.S. Appl. No. 10/549,216.
Response Dated May 4, 2009 to Official Action of Nov. 3, 2008 From the US Patent and Trademark Office Re.: U.S. Appl. No. 10/116,201.
Response Dated May 4, 2010 to Official Action of Jan. 5, 2010 From the US Patent and Trademark Office Re.: U.S. Appl. No. 11/802,685.
Response Dated Oct. 4, 2007 to Official Action of Sep. 4, 2007 From the US Patent and Trademark Office Re.: U.S. Appl. No. 95/000,032.
Response Dated Jan. 5, 2010 to Official Action of Oct. 8, 2009 From the US Patent and Trademark Office Re. U.S. Appl. No. 11/566,775.
Response Dated Apr. 6, 2010 to Official Action of Oct. 6, 2009 From the US Patent and Trademark Office Re.: U.S. Appl. No. 11/550,560.
Response Dated May 6, 2010 to Office Action Dated Jan. 8, 2010 From the State Intellectual Property Office (SIPO) of the People's Republic of China Re.: Application No. 200480012687.5.
Response Dated Feb. 7, 2010 to Official Action of Dec. 2, 2009 From the US Patent and Trademark Office Re.: U.S. Appl. No. 11/932,149.
Response Dated Feb. 7, 2010 to Official Action of Nov. 3, 2009 From the US Patent and Trademark Office Re.: U.S. Appl. No. 11/931,724.
Response Dated May 7, 2007 to Examination Report of Mar. 2, 2007 From the Government of India, Patent Office Re.: Application No. 533/CHENP/2005.
Response Dated Feb. 8, 2010 to Official Action Dated Oct. 1, 2009 From the US Patent and Trademark Office Re.: U.S. Appl. No. 10/237,263.
Response Dated Feb. 9, 2010 to Official Action of Oct. 8, 2009 From the US Patent and Trademark Office Re.: U.S. Appl. No. 10/116,201.
Response Dated Mar. 15, 2010 to Official Action of Sep. 14, 2009 From the US Patent and Trademark Office Re.: U.S. Appl. No. 11/931,889.
Response Dated Jan. 17, 2008 to Official Action of Jul. 18, 2007 From the US Patent and Trademark Office Re.: U.S. Appl. No. 10/039,845.
Response Dated Feb. 18, 2010 to Official Action of Aug. 18, 2009 From the US Patent and Trademark Office Re.: U.S. Appl. No. 10/570,576.
Response Dated Apr. 20, 2006 to Communication Pursuant of Article 96(2) EPC of Nov. 2, 2005 From the European Patent Office Re.: Application No. 97929478.2.
Response Dated Aug. 20, 2008 to Official Action of Jun. 20, 2008 From the US Patent and Trademark Office Re.: U.S. Appl. No. 90/008,689.
Response Dated May 21, 2008 to Office Action of Dec. 11, 2007 From the Japanese Patent Office Re.: Application No. 09-525055.
Response Dated Dec. 24, 2006 to Office Action of Jul. 18, 2006 From the Japanese Patent Office Re.: Application No. 10-513446.
Response Dated Dec. 25, 2006 to Notice of Reasons for Rejection of Jul. 18, 2006 From the Japanese Patent Office Re.: Application No. 09-529637.
Response Dated Jan. 25, 2007 to Examination Report of Jul. 7, 2006 From the Government of India, Patent Office Re.: Application No. 533/CHENP/2005.
Response Dated Mar. 25, 2010 to Official Action of Sep. 25, 2009 From the US Patent and Trademark Office Re.: U.S. Appl. No. 10/526,708.
Response Dated Oct. 5, 2010 to Official Action of May 5, 2010 From the US Patent and Trademark Office Re.: U.S. Appl. No. 11/884,389.
Summons to Attend Oral Proceedings Pursuant to Rule 115(1) EPC Dated Dec. 22, 2008 From the European Patent Office Re.: Application No. 97929480.8.
Supplementary European Search Report and the European Search Opinion Dated Nov. 28, 2008 From the European Patent Office Re.: Application No. 05853465.2.
Supplementary European Search Report Dated Jun. 7, 2010 From the European Patent Office Re. Application No. 04770468.9.
Supplementary Notice of Allowability Dated Nov. 22, 2006 From the US Patent and Trademark Office Re.: U.S. Appl. No. 10/804,560.
Translation of Decision of Rejection Dated Apr. 22, 2009 From the Japanese Patent Office Re.: Application No. 2004-534013.
Translation of Notice of Reasons for Rejection Dated Jul. 18, 2006 From the Japanese Patent Office Re.: Application No. 9-529637.
Translation of Notice of Reasons for Rejection Dated Apr. 27, 2010 From the Japanese Patent Office Re.: Application No. 2007-206282.
Translation of Notification of Reasons of Rejection Dated Apr. 12, 2010 From the Japanese Patent Office Re.: Application No. 2006-525265.
Translation of Office Action Dated Sep. 12, 2008 From the State Intellectual Property Office of the People's Republic of China Re.: Application No. 200480032636.9.
Blank et al. "Initial Interactions in Electromagnetic Field-Induced Biosynthesis", Journal of Cellular Physiology, 199: 359-363, 2004.
Highfill et al. "Large-Scale Production of Murine Bone Marrow Cells in an Airlift Packed Bed Bioreactor", Biotechnology and Bioengineering, 50(5): 514-520, 1996.
Holst et al. "Nervous Control of Pancreatic Endocrine Secretion in Pigs. II. The Effect of Pharmacological Blocking Agents on the Response to Vagal Stimulation", Acta Physiologica Scandinavica, 111(1): 9-14, 1981. Abstract.
Official Action Dated Dec. 20, 2011 From the US Patent and Trademark Office Re.: U.S. Appl. No. 10/039,845.

(56) References Cited

OTHER PUBLICATIONS

Response Dated Dec. 14, 2011 to Official Action of Sep. 14, 2011 From the US Patent and Trademark Office Re. U.S. Appl. No. 11/886,154.
Official Action Dated May 12, 2011 From the US Patent and Trademark Office Re.: U.S. Appl. No. 10/039,845.
Official Action Dated Jun. 13, 2011 From the US Patent and Trademark Office Re. U.S. Appl. No. 11/933,168.
Official Action Dated Jul. 21, 2010 From the US Patent and Trademark Office Re.: U.S. Appl. No. 11/802,685.
Supplementary Partial European Search Report Dated Nov. 4, 2010 From the European Patent Office Re. Application No. 04719312.3.
Official Action Dated Jan. 4, 2012 From the US Patent and Trademark Office Re. U.S. Appl. No. 11/673,812.
Official Action Dated Dec. 15, 2011 From the US Patent and Trademark Office Re. U.S. Appl. No. 12/910,943.
Response Dated Dec. 8, 2011 to Official Action of Aug. 9, 2011 From the US Patent and Trademark Office Re.: U.S. Appl. No. 11/932,149.
Response Dated Dec. 27, 2011 to Communication Pursuant to Article 94(3) EPC of Aug. 26, 2011 From the European Patent Office Re. Application No. 06759102.4.
Response Dated Apr. 10, 2011 to Official Action of Jan. 6, 2011 From the US Patent and Trademark Office Re.: U.S. Appl. No. 11/931,724.
USPTO Public Print Out of Interference File Content of Interference Dated Apr. 4, 2011 From the US Patent and Trademark Office Re. Interference No. 105,765.
USPTO Public Print Out of Interference File Content of Interference Dated Apr. 4, 2011 From the US Patent and Trademark Office Re. Interference No. 105,768.
Response Dated Sep. 30, 2010 to Official Action of Apr. 30, 2010 From the US Patent and Trademark Office Re.: U.S. Appl. No. 11/931,724.
San Mauro et al. "Nerves of the Heart: A Comprehensive Review With a Clinical Point of View", Neuroanatomy, 8: 28-31, 2009.
Response Dated Aug. 1, 2010 to Notification of Reasons of Rejection of Apr. 12, 2010 from the Japanese Patent Office Re.: Application No. 2006-525265.
Response Dated Aug. 2, 2010 to Official Action of Mar. 31, 2010 From the US Patent and Trademark Office Re.: U.S. Appl. No. 10/237,263.
Response Dated Jul. 26, 2010 to Official Action of Mar. 25, 2010 From the US Patent and Trademark Office Re.: U.S. Appl. No. 10/804,560.
Response Dated Aug. 1, 2011 to Notice of Non-Compliant Amendment of Jul. 15, 2011 From the US Patent and Trademark Office Re. U.S. Appl. No. 11/886,154.
Translation of Office Action Dated Aug. 3, 2011 From the State Intellectual Property Office (SIPO) of the People's Republic of China Re.: Application No. 200480012687.5.
Official Action Dated Sep. 14, 2011 From the US Patent and Trademark Office Re. U.S. Appl. No. 11/886,154.
Examination Report Dated Nov. 30, 2010 From the Government of India, Patent Office Re. Application No. 212/MUMNP/2006.
Office Action Dated Apr. 13, 2010 From the State Intellectual Property Office of the People's Republic of China Re. Application No. 200480027293.3 and Its Translation Into English.
Official Action Dated Dec. 15, 2010 From the US Patent and Trademark Office Re.: U.S. Appl. No. 10/804,560.
Response dated Oct. 12, 2010 to Official Action of Jun. 11, 2010 From the US Patent and Trademark Office Re.: U.S. Appl. No. 11/932,064.
Response Dated Dec. 13, 2010 to Official Action of Jun. 11, 2010 From the US Patent and Trademark Office Re.: U.S. Appl. No. 11/550,560.
Response Dated Dec. 13, 2010 to Official Action of Oct. 13, 2010 From the US Patent and Trademark Office Re.: U.S. Appl. No. 11/919,491.
Response Dated Nov. 22, 2010 to Official Action of Jul. 21, 2010 From the US Patent and Trademark Office Re.: U.S. Appl. No. 11/802,685.

Response Dated Oct. 28, 2010 to Official Action of Jun. 28, 2010 From the US Patent and Trademark Office Re.: U.S. Appl. No. 11/931,889.
Official Action Dated Apr. 14, 2011 From the US Patent and Trademark Office Re.: U.S. Appl. No. 11/932,149.
Official Action Dated Apr. 28, 2011 From the US Patent and Trademark Office Re.: U.S. Appl. No. 11/931,889.
Response Dated Apr. 20, 2011 to Official Action of Mar. 22, 2011 From the US Patent and Trademark Office Re. U.S. Appl. No. 11/886,154.
Supplemental Response Dated Apr. 18, 2011 to Response of Apr. 10, 2011 to Official Action of Jan. 6, 2011 From the US Patent and Trademark Office Re.: U.S. Appl. No. 11/931,724.
Communication Pursuant to Article 94(3) EPC Dated Aug. 11, 2010 From the European Patent Office Re. Application No. 99931435.4.
Official Action Dated Jan. 6, 2011 From the US Patent and Trademark Office Re.: U.S. Appl. No. 11/931,724.
Official Action Dated Mar. 6, 2009 From the US Patent and Trademark Office Re.: U.S. Appl. No. 11/931,889.
Official Action Dated Oct. 13, 2010 From the US Patent and Trademark Office Re.: U.S. Appl. No. 11/919,491.
Official Action Dated Aug. 31, 2010 From the US Patent and Trademark Office Re.: U.S. Appl. No. 11/550,560.
Request for Ex Parte Reexamination of U.S. Patent No. 6,236,887—IDS Submitted Sep. 29, 2008 From the US Patent and Trademark Office Re.: U.S. Appl. No. 90/008,707.
Response Dated Jun. 7, 2010 to Official Action of Jan. 6, 2010 From the US Patent and Trademark Office Re. U.S. Appl. No. 11/933,168.
Response Dated Jul. 13, 2010 to Notice of Reasons for Rejection of Apr. 27, 2010 From the Japanese Patent Office Re.: Application No. 2007-206282.
Adeghate et al. "Effect of Electrical Field Stimulation on Insulin and Glucagon Secretion From the Pancreas of Normal and Diabetic Rats", Hormone and Metabolic Research, 33(5): 281-289, May 2001. Abstract.
Bergsten et al. "Synchronous Oscillations of Cytoplasmic Ca2+ and Insulin Release in Glucose-Stimulated Pancreatic Islets", The Journal of Biological Chemistry, 269(12): 8749-8753, Mar. 25, 1994.
Burfeind et al "The Effects of Mechanical Cardiac Stabilization on Left Ventricular Performance", Europcari Journal of Cardio-Thoracic Surgery, 14: 285-289, 1998.
Devedeux et al. "Uterine Electromyography: A Critical Review", American Journal of Obstetric Gynecology, 169(6): 1636-1653, 1993.
Fromer et al. "Ultrarapid Subthreshold Stimulation for Termination of Atriventricular Node Reentrant Tachycardia", Journal of the American College Cardiology, 20: 879-883, 1992.
Gold et al. "Evidence That Glucose 'Marks' Beta Cells Resulting in Preferential Release of Newly Synthesized Insulin", Science, 218(4567): 56-58, Oct. 1, 1982. Abstract.
Gomis et al. "Oscillatory Patterns of Electrical Activity in Mouse PancreaticIslets of Langerhans Recorded in Vivo", Pfl?gers Archiv European Journal of Physiology, 432(3): 510-515, 1996.
Hinke et al. "Dipeptidyl Peptidase IV (DPIV/CD26) Degradation of Glucagon. Characterization of Glucagon Degradation Products and DPIV-Resistant Analogs", The Journal of Biological Chemistry, 275(6): 3827-3834, Feb. 11, 2000.
Holst et al. "Nervous Control of Pancreatic Endocrine Secretion in Pigs. I. Insulin and Glucagon Responses to Electrical Stimulation of the Vagus Nerves", Acta Physiologica Scandinavica, 111(1): 1-7, Jan. 1981. Abstract.
Horner et al. "Electrode for Recording Direction of Activation, Conduction Velocity and Monophasic Action Potential of Myocardium", American Journal of Physiology, 272(4): H1917-H1927, 1997. Abstract.
Jaremko et al. "Advances Towards the Implantable Artifical Pancreas for Treatment of Diabetes", Diabetes Care, 21(3): 444-450, 1998.
Kurose et al. "Glucagon, Insulin and Somatostatin Secretion in Response to Sympathetic Neural Activation in Streptozotocin-Induced Diabetic Rats. A Study With the Isolated Perfused Rat Pancreas in Vitro", Diabetologia, 35(11): 1035-1041, Nov. 1992. Abstract.

(56) References Cited

OTHER PUBLICATIONS

Magnus et al. "Model of ?—Cell Mitochondrial Calcium Handling and Electrical Activity. II. Mitochondrial Variables", American Journal of Physiology, Cell Physiology, 274(43): C1174-C1184, 1998.
Meurer et al. "Properties of Native and in Vitro Glycosylated Forms of the Glucogan-Like Peptide-1 Receptor Antagonist Exendin(9-39)", Metabolism: Clinical and Experimental, 48(6): 716-724, Jun. 1999. Abstract.
Misler et al. "Electrophysiology of Stimulus-Secretion Coupling in Human Beta-Cells", Diabetes, 41(10): 1221-1228, Oct. 1992. Abstract.
Nadal et al. "Homologous and Heterologous Asynchronicity Between Identified ?-, ?- and ?- Cells Within Intact Islets of Langerhans in the Mouse", Journal of Physiology, 517(Pt.1): 85-93, 1999.
Ohinata et al. "Proadrenomedullin N-Terminal 20 Peptide (PAMP) Elevates Blood Glucose Levels Via Bombesin Receptor in Mice", FEBS Letters, 473(2): 207-211, May 2000. Abstract.
P?rksen et al. "Section 6: Pulsatile and Phasic Insulin Release in Normal and Diabetic Man. Pulsatile Insulin Secretion: Detection, Regulation, and Role in Diabetes", Diabetes, 51(Suppl.1): S245-S254, Feb. 2002.
Patti et al. "Islets of Langerhans Generate Wavelike Electric Activity Modulated by Glucose Concentration", Diabetes, 45(5): 595-601, May 1996. Abstract.
Park et al. "Significant Cholinergic Role in Secretin-Stimulated Exocrine Secretion in Isolated Rat Pancreas", American Journal of Physiology, AJP—Gastrointestinal and Liver Physiology, 274(2): G413-G418, Feb. 1998.
Pokrovsky et al. "Physiology of Man", 1: 82-83, 94, 2: 42, 54.
Rivera et al. "Regulation of Protein Secretion Through Controlled Aggregation in the Endoplasmic Reticulum", Science, 287(5454): 826-830, Feb. 4, 2000. Abstract.
Schirra et al. "Exendin(9-39) Amide Is an Antagonist of Glucagon-Like Peptide-1(7-36) Amide in Humans", Journal of Clinical Investigation, 101(7): 1421-1430, Apr. 1998.
Schirra et al. "Mechanisms of the Antidiabetic Action of Subcutaneous Glucagon-Like Peptide-1 (17-36) Amide in Non-Insulin Dependent Diabetes Mellitus", Journal of Endocrinology Ltd., 156(1): 177-186, Jan. 1998. Abstract.
Serre et al. "Exendin-(9-39) Is an Inverse Agonist of the Murine Glucagon-Like Peptide-1 Receptor: Implications for Basal Intracellular Cyclic Adenosine 3',5'-Monophosphate -Levels and ?-Cells Glucose Competence", Endocrinology, 139(11): 4448-4454, 1998.
Shah et al. "Impact of Lack of Suppression of Glucagon on Glucose Tolerance in Humans", American Journal of Physiology, AJP—Endocrinology and Metabolism, 277(2 Pt.1): E283-E290, 1999.
Shmit et al. "Physiology of Man", Moscow Medicine, Mir, 1: 78, 1996.
Shuba et al. "Physiology of Vessel Smooth Muscles", Kiev Naukova Dumka, 142: 11-15, 142, 1988.
Singh et al. "Effects of Islet Hormones on Nerve-Mediated and Acetylcholine-Evoked Secretory Responses in the Isolated Pancreas of Normal and Diabetic Rats", International Journal of Molecular Medicine, 1(3): 627-634, Mar. 1998. Abstract.
Soria et al. "Cytosolic Calcium Oscillations and Insulin Release in Pancreatic Islets of Langerhans", Diabetes & Metabolism, 24: 37-40, 1998.
Valdeolmillos et al. "In Vivo Synchronous Membrane Potential Oscillations in Mouse Pancreatic Beta-Cells: Lack of Co-Ordination Between Islets", Journal of Physiology, 493(1): 9-18, 1996.
Van Riper et al. "Electrical Field Stimulation-Mediated Relaxation of a Rabbit Middle Cerebral Artery. Evidence of a Cholinergic Endothelium-Dependent Component", Circulation Research, 70(6): 1104-1112, Jun. 1992.
Wang et al. "Islet Amyloid Polypeptide Tonally Inhibits ?-, ?-, and ?-Cell Secretion in Isolated Rat Pancreatic Islets", American Journal of Physiology, AJP—Endocrinology and Metabolism, 276(1 Pt.1): E19-E24, 1999.
Wright et al. "Structure of Fab hGR-2 F6, a Competitive Antagonist of the Glucagon Receptor", Acta Crystallographica, Section D, Biological Crystallography, 56(Pt.5): 573-580, May 2000. Abstract.
Yonemura et al. "Amelioration of Diabetes Mellitus in Partially Depancreatized Rats by Poly(ADP-Ribose) Synthetase Inhibitors. Evidence of Islet B-Cell Regeneration", Diabetes, 33(4): 401-404, Apr. 1984. Abstract.
Response in Conjunction With an RCE Dated Jul. 18, 2010 to Official Action Dated Feb. 4, 2010 From the US Patent and Trademark Office Re.: U.S. Appl. No. 10/039,845.
Response in Conjunction With an RCE Dated Jul. 21, 2010 to Official Action of Feb. 4, 2010 From the US Patent and Trademark Office Re.: U.S. Appl. No. 10/039,845.
Supplemental Response Dated Mar. 28, 2010 After an Interview of Mar. 4, 2010 From the US Patent and Trademark Office Re. U.S. Appl. No. 10/237,263.
Response Dated Jul. 27, 2010 to Communication Pursuant to Article 94(3) EPC of Jan. 27, 2010 From the European Patent Office Re. Application No. 07110023.4.
Response Dated Sep. 27, 2010 to Official Action of Apr. 27, 2010 From the US Patent and Trademark Office Re.: U.S. Appl. No. 10/570,576.
Official Action Dated Nov. 8, 2011 From the US Patent and Trademark Office Re.: U.S. Appl. No. 11/931,889.
Response Dated Dec. 8, 2011 to Office Action of Aug. 3, 2011 From the State Intellectual Property Office (SIPO) of the People's Republic of China Re.: Application No. 200480012687.5.
Notice of Non-Compliant Amendment Dated Dec. 12, 2011 From the US Patent and Trademark Office Re. U.S. Appl. No. 11/792,811.
Official Action Dated Jan. 6, 2012 From the US Patent and Trademark Office Re. U.S. Appl. No. 11/933,168.
Official Action Dated Jan. 18, 2012 From the US Patent and Trademark Office Re. U.S. Appl. No. 11/886,154.
Notice of Allowance Dated Jan. 14, 2011 From the US Patent and Trademark Office Re.: U.S. Appl. No. 11/550,560.
Official Action Dated Jan. 3, 2011 From the US Patent and Trademark Office Re.: U.S. Appl. No. 11/932,149.
Official Action Dated Jan. 24, 2011 From the US Patent and Trademark Office Re.: U.S. Appl. No. 11/919,491.
Official Action Dated Sep. 29, 2010 From the US Patent and Trademark Office Re. U.S. Appl. No. 11/933,168.
Response Dated Feb. 3, 2011 to Official Action of Jan. 3, 2011 From the US Patent and Trademark Office Re.: U.S. Appl. No. 11/932,149.
Response Dated Feb. 7, 2011 to Official Action of Oct. 5, 2010 From the US Patent and Trademark Office Re.: U.S. Appl. No. 10/039,845.
Response Dated Feb. 14, 2011 to Official Action Dated Jan. 13, 2011 From the US Patent and Trademark Office Re.: U.S. Appl. No. 11/931,889.
Response Dated Jan. 31, 2011 to Official Action of Sep. 29, 2010 From the US Patent and Trademark Office Re. U.S. Appl. No. 11/933,168.
Hammond et al. "Motor Innervation of the Cricopharyngeus Muscle by the Recurrent Lanryngeal Nerve", Journal of Applied Physiology, JAP, 83: 89-94, 1997.
Sutton et al. "The Foundation of Cardiac Pacing, Part 1: An Illustrated Practical Guide to Basic Pacing", The Bakken Research Center Series, Chap.4: 50-59, 1991.
Official Action Dated Jan. 6, 2010 From the US Patent and Trademark Office Re. U.S. Appl. No. 11/933,168.
Official Action Dated Mar. 22, 2011 From the US Patent and Trademark Office Re. U.S. Appl. No. 11/886,154.
Response Dated Oct. 11, 2011 to Official Action of May 12, 2011 From the US Patent and Trademark Office Re.: U.S. Appl. No. 10/039,845.
Response Dated Aug. 26, 2010 to Official Action of May 26, 2010 From the US Patent and Trademark Office Re.: U.S. Appl. No. 11/318,845.
Official Action Dated Oct. 11, 2011 From the US Patent and Trademark Office Re.: U.S. Appl. No. 11/919,491.
Notice of Allowance Dated Jan. 25, 2013 From the US Patent and Trademark Office Re.: U.S. Appl. No. 11/919,491.
Official Action Dated Feb. 15, 2012 From the US Patent and Trademark Office Re. U.S. Appl. No. 11/802,685.

(56) References Cited

OTHER PUBLICATIONS

Office Action Dated Jan. 18, 2012 From the State Intellectual Property Office (SIPO) of the People's Republic of China Re.: Application No. 200480012687.5 and Its Translation Into English.
Examination Report Dated Feb. 20, 2013 From the Government of India, Patent Office, Intellectual Property Building Re. Application No. 5571/CHENP/2007.
Kanno et al. "Establishment of a Simple and Practical Procedure Applicable to Therapeutic Angiogenesis", Circulation, 99: 2682-2687, 1999.
Office Action Dated Nov. 2, 2007 From the Patent Office of the People's Republic of China Re.: Application No. 2004800009336.9.
Official Action Dated Dec. 5, 2008 From the US Patent and Trademark Office Re.: U.S. Appl. No. 11/550,560.
Official Action Dated Dec. 8, 2008 From the US Patent and Trademark Office Re.: U.S. Appl. No. 10/804,560.
Official Action Dated Dec. 24, 2008 From the US Patent and Trademark Office Re.: U.S. Appl. No. 10/237,263.
Supplementary European Search Report and the European Search Opinion Dated Nov. 28, 2008 From the European Patent Office Re.: Application No. 006759102.4.
Translation of the Examination Report Dated Apr. 3, 2008 From the Government of India, Patent Office Re.: Application No. 1821/CHENP/2005.
Applicant-initiated interview Summary Dated Nov. 28, 2012 From the US Patent and Trademark Office Re.: U.S. Appl. No. 11/919,491.
Applicant-initiated Interview Summary Dated Apr. 11, 2013 From the US Patent and Trademark Office Re. U.S. Appl. No. 11/673,812.
Examination Report Dated Feb. 27, 2013 From the Government of India, Patent Office, Intellectual Property Building Re. Application No. 2014/CHENP/2008.
Advisory Action Before the Filing of an Appeal Brief Dated May 9, 2013 From the US Patent and Trademark Office Re. U.S. Appl. No. 11/673,812.
Butter et al. "Enhanced Inotropic State of the Failing Left Ventricle by Cardiac Contractility Modulation Electrical Signals Is Not Associated With Increased Myocardial Oxygen Consumption", Journal of Cardiac Failure, 13(2): 137-142, 2007.
Lawo et al. "Electrical Signals Applied During the Absolute Refractory Period. An Investigational Treatment for Advanced Heart Failure in Patients With Normal QRS Duration", Journal of the American College of Cardiology, 46(12): 2229-2236, 2005.
Neelagaru et al. "Nonexcitatory, Cardiac Contractility Modulation Electrical Impulses: Feasibility Study for Advanced Heart Failure in Patients With Normal QRS Duration", Heart Rythm, 3(10): 1140-1147, 2006.
Notice of Allowance Dated May 15, 2012 From the US Patent and Trademark Office Re.: U.S. Appl. No. 11/932,149.
Notice of Allowance Dated May 16, 2012 From the US Patent and Trademark Office Re. U.S. Appl. No. 11/886,154.
Official Action Dated May 29, 2013 From the US Patent and Trademark Office Re. U.S. Appl. No. 13/662,775.
Notice of Allowance Dated Jun. 20, 2012 From the US Patent and Trademark Office Re. U.S. Appl. No. 11/933,168.
Corrected Notice of Allowability Dated Jul. 13, 2012 From the US Patent and Trademark Office Re. U.S. Appl. No. 11/933,168.
Notice of Allowability Dated Jul. 13, 2012 From the US Patent and Trademark Office Re. U.S. Appl. No. 11/933,168.
Notice of Allowance Dated Jul. 16, 2012 From the US Patent and Trademark Office Re. U.S. Appl. No. 11/931,889.
Notice of Allowance Dated Jul. 18, 2012 From the US Patent and Trademark Office Re.: U.S. Appl. No. 11/931,724.
Official Action Dated Jul. 3, 2012 From the US Patent and Trademark Office Re. U.S. Appl. No. 12/910,943.
Official Action Dated May 10, 2012 From the US Patent and Trademark Office Re. U.S. Appl. No. 10/599,015.
Notice of Allowance Dated Jan. 14, 2011 From the US Patent and Trademark Office Re. U.S. Appl. No. 11/550,560.
Notice of Allowance Dated Aug. 31, 2012 From the US Patent and Trademark Office Re. U.S. Appl. No. 12/910,943.
Official Action Dated Aug. 27, 2012 From the US Patent and Trademark Office Re.: U.S. Appl. No. 11/919,491.
Official Action Dated Feb. 17, 2012 From the US Patent and Trademark Office Re.: U.S. Appl. No. 11/932,149.
Official Action Dated Dec. 21, 2012 From the US Patent and Trademark Office Re. U.S. Appl. No. 11/673,812.
Advisory Action Before the Filing of an Appeal Brief Dated Mar. 22, 2012 From the US Patent and Trademark Office Re. U.S. Appl. No. 11/886,154.
Bers "Excitation-Contracting Coupling", Excitation-Contraction Coupling and Cardiac Contractile Force, 2nd Ed., Chap.8: 203-407, 2001. (Part I).
Bers "Excitation-Contracting Coupling", Excitation-Contraction Coupling and Cardiac Contractile Force, 2nd Ed., Chap.8: 203-407, 2001. (Part II).
Bers "Excitation-Contracting Coupling", Excitation-Contraction Coupling and Cardiac Contractile Force, 2nd Ed., Chap.8: 203-407, 2001. (Part III).
Bers "Excitation-Contracting Coupling", Excitation-Contraction Coupling and Cardiac Contractile Force, 2nd Ed., Chap.8: 203-407, 2001. (Part IV).
Bers "Excitation-Contracting Coupling", Excitation-Contraction Coupling and Cardiac Contractile Force, 2nd Ed., Chap.8: 203-407, 2001. (Part V).
Bers "Excitation-Contracting Coupling", Excitation-Contraction Coupling and Cardiac Contractile Force, 2nd Ed., Chap.8: 203-407, 2001. (Part VI).
Bers "Excitation-Contracting Coupling", Excitation-Contraction Coupling and Cardiac Contractile Force, 2nd Ed., Chap.8: 203-407, 2001. (Part VII).
Knisley et al. "Prolongation and Shortening of Action Potentials by Electrical Shocks in Frog Ventricular Muscle", American Journal of Physiology, 266(6): H2348-H2358, 1994.
Examination Report Dated Jan. 9, 2014 From the Government of India, Patent Office, Intellectual Property Building Re. Application No. 5571/CHENP/2007.
Official Action Dated Jan. 14, 2014 From the US Patent and Trademark Office Re. U.S. Appl. No. 10/039,845.
Notice of Non-Compliant Amendment Dated Jun. 17, 2013 From the US Patent and Trademark Office Re. U.S. Appl. No. 10/039,845.
Official Action Dated Sep. 10, 2013 From the US Patent and Trademark Office Re. U.S. Appl. No. 09/980,748.
Examination Report Dated Sep. 17, 2013 From the Government of India, Patent Office, Intellectual Property Building Re. Application No. 5571/CHENP/2007.
Examination Report Dated Dec. 30, 2013 From the Government of India, Patent Office, Intellectual Property Building Re. Application No. 5571/CHENP/2007.
Hearing Notice in Reference of Application No. 5571/CHENP/2007 Dated Mar. 6, 2014 From the Government of India, Patent Office, Intellectual Property Building Re. Application No. 5571/CHENP/2007.
Official Action Dated Oct. 16, 2013 From the US Patent and Trademark Office Re. U.S. Appl. No. 13/970,647.
Babsky et al. Translation of Physiology of Man, Moscow Medicine, P.115, 348-351, 376, Extracts.
Official Action Dated Apr. 15, 2014 From the US Patent and Trademark Office Re. U.S. Appl. No. 13/970,647.
Communication Pursuant to Article 94(3) EPC Dated Aug. 26, 2011 From the European Patent Patent Office Re. Application No. 06759102.4.
Communication Pursuant to Article 94(3) EPC Dated Aug. 26, 2011 From the European Patent Office Re.: Application No. 05853465.2.
Official Action Dated Oct. 10, 2008 From the US Patent and Trademark Office Re. U.S. Appl. No. 09/980,748.
Official Action Dated Sep. 11, 2009 From the US Patent and Trademark Office Re. U.S. Appl. No. 09/980,748.
Official Action Dated May 21, 2007 From the US Patent and Trademark Office Re. U.S. Appl. No. 09/980,748.
Official Action Dated Dec. 23, 2010 From the US Patent and Trademark Office Re. U.S. Appl. No. 09/980,748.
Official Action Dated Feb. 28, 2008 From the US Patent and Trademark Office Re. U.S. Appl. No. 09/980,748.

(56) References Cited

OTHER PUBLICATIONS

Official Action Dated Apr. 29, 2009 From the US Patent and Trademark Office Re. U.S. Appl. No. 09/980,748.
Official Action Dated Aug. 30, 2006 From the US Patent and Trademark Office Re. U.S. Appl. No. 09/980,748.
Notice of Non-Compliant Amendment Dated Jul. 15, 2011 Prom the US Patent and Trademark Office Re. U.S. Appl. No. 11/886,154.
Response Dated Jul. 27, 2011 to Official Action of Apr. 28, 2011 From the US Patent and Trademark Office Re.: U.S. Appl. No. 11/931,889.
Response Dated Jun. 29, 2011 to Notice of Non-Compliant Amendment of Jun. 1, 2011 From the US Patent and Trademark Office Re. U.S. Appl. No. 11/886,154.
Response Dated Jul. 31, 2011 to Official Action of Apr. 14, 2011 From the US Patent and Trademark Office Re.: U.S. Appl. No. 11/932,149.
Sutton et al. "What Is a Pacemaker?", The Foundations of Cardiac Pacing, Part I: An Illustrated Practical Guide to Basic Pacing, Chap. 4.5: 73-74, 1991.
Webster "Electrodes, Leads, and Biocompatibility", Design of Cardiac Pacemakers, IEEE Press, p. 141-144, 1995.
Applicant-Initiated Interview Summary Dated Dec. 11, 2013 From the US Patent and Trademark Office Re. U.S. Appl. No. 13/970,647.
Notification of Reexamination Dated Apr. 4, 2014 From the State Intellectual Property Office of the People's Republic of China Re. Application No. 200480012687.5 and Its Translation Into English.

* cited by examiner

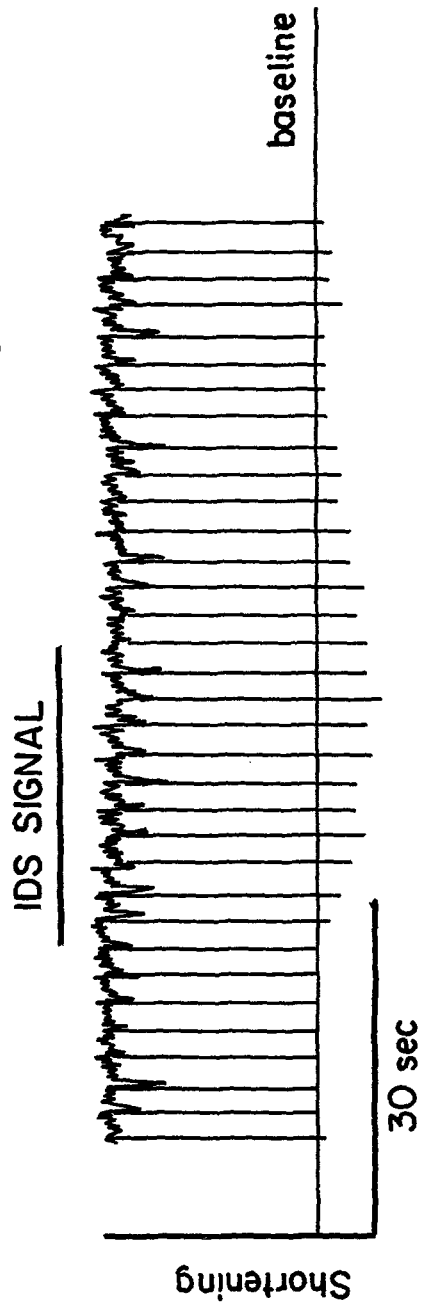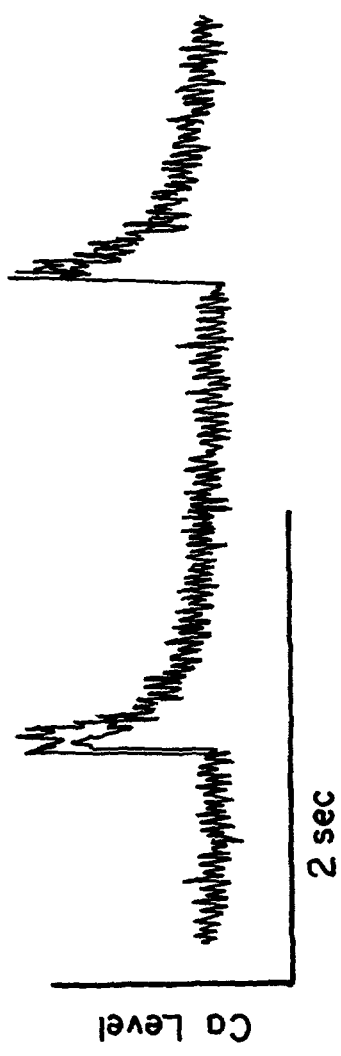

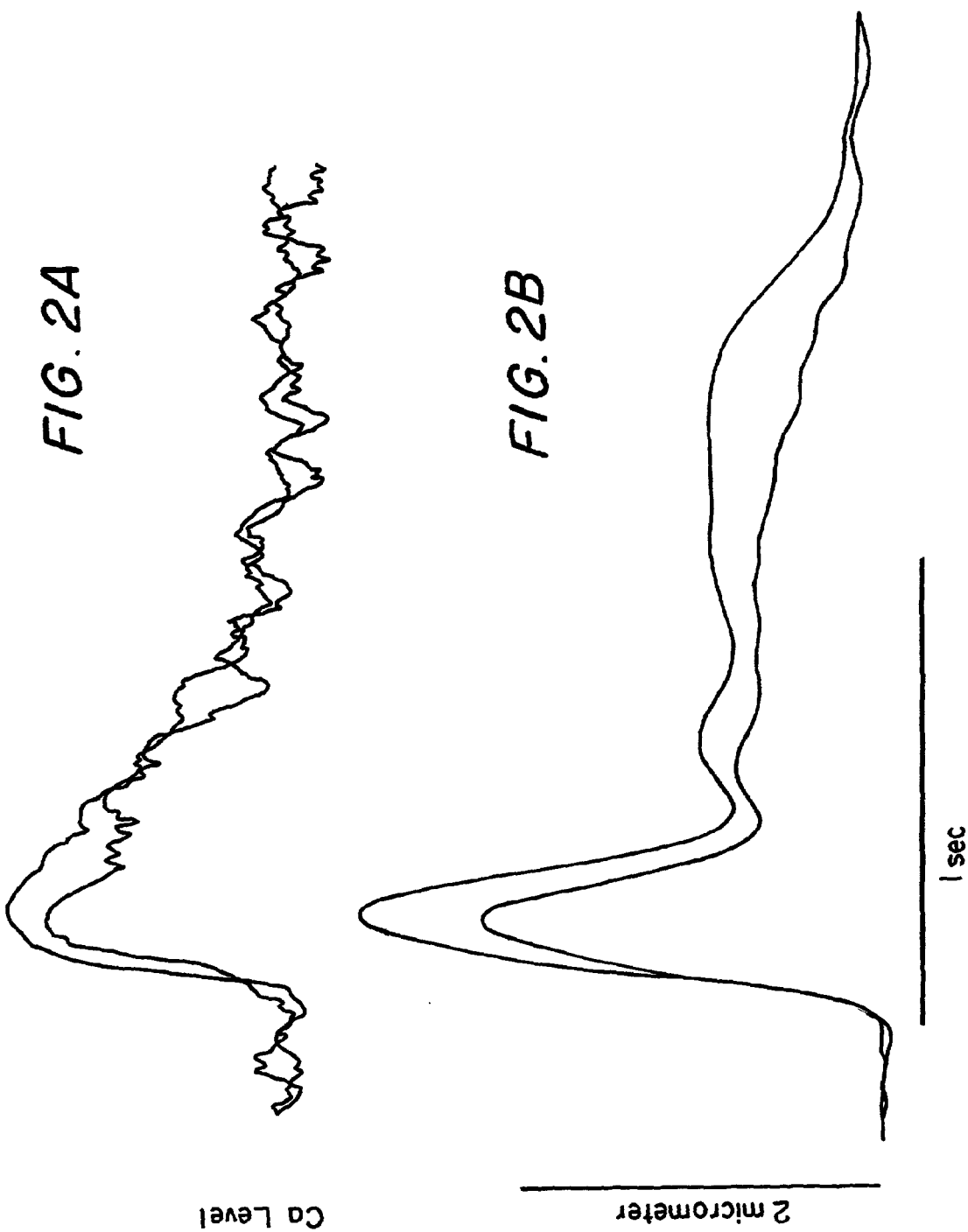

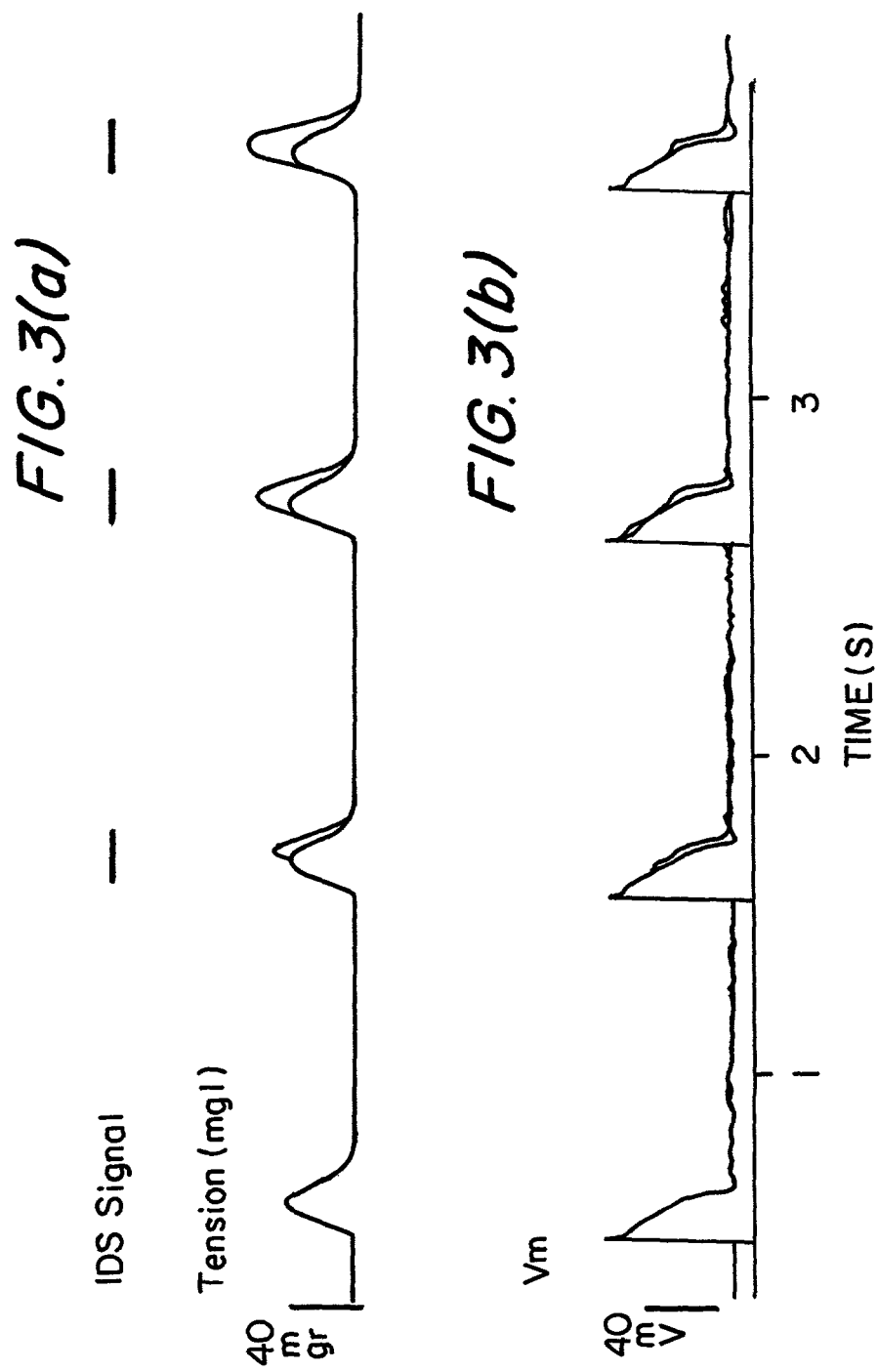

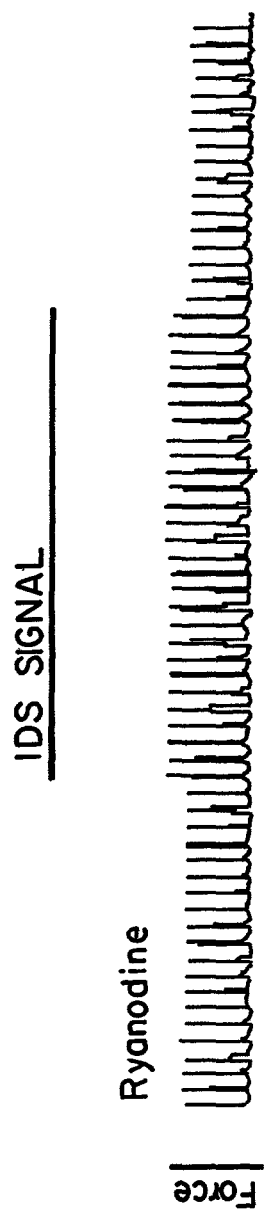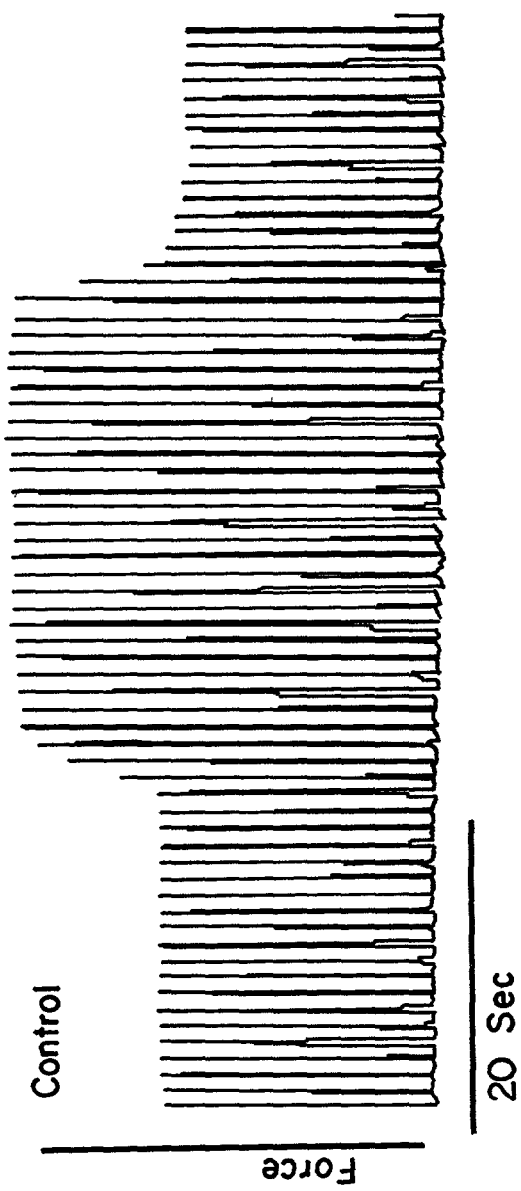
FIG. 4(b)
FIG. 4(a)

MODULATION OF INTRACELLULAR CALCIUM CONCENTRATION USING NON-EXCITATORY ELECTRICAL SIGNALS APPLIED TO THE TISSUE

CROSS-REFERENCE TO RELATED APPLICATION

This application is a continuation-in-part of co-pending U.S. patent application Ser. No. 10/039,845, filed Oct. 23, 2001, which is in turn a continuation of U.S. patent application Ser. No. 09/563,544, filed May 1, 2000, now U.S. Pat. No. 6,363,279, which in turn is a continuation of U.S. patent application Ser. No. 09/101,723, filed Aug. 13, 1998, now U.S. Pat. No. 6,317,631, which is the National Stage of International Application No. PCT/IL97/00012, filed Jan. 8, 1997, which is based upon and claims the benefit of U.S. patent application Ser. No. 08/595,365, filed Feb. 1, 1996, now U.S. Pat. No. 5,738,096, U.S. Provisional Patent Application Ser. No. 60/009,769, filed Jan. 11, 1996, U.S. Provisional Patent Application Ser. No. 60/011,117, filed Feb. 5, 1996, and U.S. Provisional Patent Application Ser. No. 60/026,392, filed Sep. 16, 1996; and this application is a continuation of International Application No. PCT/IB00/01523, filed Oct. 4, 2000, which in turn claims the benefit of U.S. Provisional Patent Application Ser. No. 60/157,511, filed Oct. 4, 1999, which is assigned to the assignee of the present patent application and is incorporated herein by reference.

FIELD OF THE INVENTION

This invention relates generally to invasive devices and methods for treatment of the heart, including devices and methods for stimulation of the heart muscle. More particularly, this invention relates to control of cellular tissue, specifically the modulation of intracellular calcium concentration in cardiac muscle cells.

BACKGROUND OF THE INVENTION

Cardiac insufficiency, characterized inter alia by a reduction in cardiac output, is a common, well-known and well-documented heart malfunction. It develops as a result of congenital defects or as an end-effect of many diseases. Cardiac output, i.e., the output of the heart per unit time, is the product of stroke volume and heart rate. Hence, variations in cardiac output can be produced by changes in cardiac rate or stroke volume. The stroke volume can be influenced, for example, by changing the strength of cardiac contraction, by changing the length of the cardiac muscle fibers, and by changing contractility of cardiac muscle independent of fiber length. The heart rate and rhythm influence the cardiac output both directly and indirectly, since changes in the rate and rhythm also affect myocardial contractility.

The human body normally regulates the cardiac output in response to body needs by changing the heart rate, as during physical exercise, and/or by adapting the stroke volume. Under pathological conditions, however, some of the normal regulatory mechanisms may be damaged. For example, heart tissue damaged due to-myocardial infarct typically cannot sustain normal pumping function, leading to a reduction in stroke volume, and hence of cardiac output. The body may react to such a reduction by increasing the heart rate, thus imposing long term strain on the heart muscles, leading in more severe cases to heart failure. There is thus a need for devices and treatments that can regulate the cardiac output, so as to compensate for the deficiencies in the normal regulation mechanisms.

In response to this need, modern cardiology has developed means to control various parameters associated with the heart's operation. Pharmaceuticals, for example, may be used to influence the conduction velocity, excitability, contractility and duration of the refractory period of the heart tissue. These pharmaceuticals are used to treat arrhythmia, enhance cardiac output and prevent fibrillation. Pharmaceuticals are generally limited in effectiveness in that they affect both healthy and diseased segments of the heart, usually, with a relatively low precision. They frequently also have unwanted side-effects.

A special kind of control can be achieved using implantable electronic devices, which provide excitatory electrical stimulation to the heart to control directly the heart rate and/or rhythm. For example, a pacemaker, an electronic device which is typically implanted in the heart to support the heart's electrical excitation system or to bypass a blocked portion of the conduction system. Another type of cardiac electronic device is a defibrillator, which senses fibrillation in the heart and applies a high voltage impulse to "reset" the heart. While electronic pacemakers can control the heart rate, however, they are limited in their capacity to enhance cardiac output, and they are known to reduce stroke volume in at least some instances. Defibrillators are useful in treating arrhythmia when it occurs (although they are painful to the patient and traumatic to the heart), but they provide no long-term amelioration of cardiac insufficiency.

Thus, none of the treatments known in the art allow effective, long-term regulation of cardiac output. PCT patent application PCT/IL97/00012, published as WO 97/25098, to Ben-Haim et al., which is incorporated herein by reference, describes methods for modifying the force of contraction of at least a portion a heart chamber by applying a non-excitatory electric field to the heart at a delay after electrical activation of the portion. The non-excitatory field is such as does not induce new activation potentials in cardiac muscle cells, but rather modifies the cells' response to the activation.

OBJECTS OF THE INVENTION

It is an object of some aspects of the present invention to provide improved methods and apparatus for controlling calcium concentration in biological tissue.

It is also an object of the present invention to provide methods and apparatus for modulating intracellular calcium concentration in cardiac tissue.

It is a further object of the present invention to provide methods and apparatus for modulating cardiac contractibility.

These and other objects of the invention will become more apparent form the discussion below.

SUMMARY OF THE INVENTION

In preferred embodiments of the present invention, a controller comprises a non-excitatory stimulation probe, including one or more non-excitatory stimulation electrodes, at least one sensor, preferably a sensing electrode; and electronic control circuitry, coupled to the stimulation probe and sensor. The stimulation electrodes and, preferably, the sensor are implemented in the heart. Alternatively, a sensing electrode may be placed on a body surface. The circuitry receives signals from the sensor, indicative of the heart's activity, and responsive thereto, drives the stimulation electrodes to provide non-excitatory electrical stimulation to the heart. A non-excitatory electrical field, current or voltage is passed through biological tissue, such as cardiac tissue, or in its proximity, resulting in either changing trans-membranal calcium ion fluxes or and/or intracellular stores content.

The term "non-excitatory electrical stimulation" ("IDS") in the context of the present patent application and in the claims, refers to electrical pulses that do not induce new activation potentials to propagate in cardiac muscle cells. Rather, such pulses generally affect the response of the heart muscle to the action potentials, possibly by modulating cell contractility within selected segments of the cardiac muscle.

In any case, the effect of the device on intracellular calcium concentration is preferably regulated by changing the timing of the non-excitatory stimulation pulse relative to the heart's activity, preferably relative to the heart's local electrical activity or ECG signals received by the sensing electrode, and/or by changing other pulse characteristics, such as voltage, current, duration, polarity, waveform and frequency of the waveform. Preferably, the device senses the heart's sinus rhythm and applies and synchronizes the stimulation pulse relative thereto, preferably with a delay before the onset of the stimulation pulse. Additionally, the circuitry may analyze the signals, for example, to determine the QT interval, so as to adjust the stimulation pulses responsive thereto. Alternatively, when the heart's rhythm is irregular, due to ventricular premature beats (VPB's) or other cardiac arrhythmias, the device preferably identifies and analyzes the irregularity, using signal processing methods known in the art, and adjusts or withholds the stimulation pulse accordingly.

In some preferred embodiments of the present invention the control circuitry is contained within a console external to the body, and the electrodes are fed percutaneously into the subject's vascular system, for example, through the femoral artery, and are implanted in the heart. Such embodiments are useful particularly in short-term therapy to regulate and stabilize the subject's hemodynamics following an insult or trauma, for example, open heart surgery or MI.

In alternative preferred embodiments of the present invention, the electronic control circuitry is contained within a miniaturized, implantable case, similar to pacemaker cases known in the art.

In some preferred embodiments of the present invention, the non-excitatory stimulation electrodes known in the art, such as pacing or electrophysiology electrodes. Preferably, the stimulation electrodes comprise large-area carbon electrodes or any other metal electrodes such as titanium nitrate, iridium oxide, most preferably vitreous carbon, or alternatively, pyro-carbon. Both types of carbon materials are known for their compatibility with heart tissue, in-vivo durability and excellent electrical properties, including high electrical conductivity. Thus, they allow a relatively high electrical current to be delivered to a relatively large segment of the heart tissue, without inducing electrical excitation.

In other preferred embodiments of the present invention, the non-excitatory stimulation electrodes are inserted into one of the blood vessels of the heart, preferably into the coronary sinus, or alternatively, into a coronary artery.

In another preferred embodiment of this type, different stimulation pulses are applied to respective ones or groups of the plurality of stimulation electrodes. Preferably, the different stimulation pulses are applied to the respective electrodes with a predetermined delay between the different pulses. The delay may be varied so as to achieve a desired hemodynamic effect, for example, to maximize the increase in stroke volume.

In still other such preferred embodiments, the positions of the plurality of stimulation electrodes and/or characteristics of the stimulation pulses applied thereto are optimized responsive to clinical characteristics of the heart. Preferably, before insertion of the electrodes, a map of the heart is produced, for example, an electrophysiological map, as described in U.S. Pat. No. 5,568,809, or a phase-dependent geometrical map, as described in PCT Patent Application PCT/IL97/00011, both of which are incorporated herein by reference. Preferably, the map includes information regarding the viability of the heart tissue, for example, based on local contractility or electrical activity. The non-excitatory stimulation electrodes are then positioned responsive to the map.

Preferably, applying the IDS signal includes conveying electrical energy to cells of the heart, such that action potentials are generally not generated in the cells responsive to the application of the non-excitatory signal.

Further preferably, the IDS signal is applied to improve hemodynamic performance of the heart. Preferably, the IDS signal is applied in order to increase contractility of the heart or, alternatively or additionally, to increase systolic pressure generated by the heart.

In a preferred embodiment, applying the IDS signal includes sensing physiological variables and applying the signal responsive thereto. Preferably, sensing the variable includes detecting an electrical depolarization wave in the tissue. Alternatively, sensing the variable includes sensing a hemodynamic parameter. Preferably, applying the pacing pulses include controlling application of the pacing pulses responsive to the variable, wherein controlling the application of the pacing pulses includes making a transition from a first stimulation mode to a second stimulation mode responsive to the variable.

There is also provided, in accordance with a preferred embodiment of the present invention, apparatus for stimulating cardiac tissue, including:

a plurality of electrodes, which are placed at multiple sites in at least two different chambers of the heart; and an electrical control unit, which applies pacing pulses to two or more of the electrodes at respective pacing sites in the at least two different chambers, and which applies an IDS signal to at least one of the electrodes in a vicinity of one or more of the pacing sites following application of the pacing pulse at the site.

Preferably, the at least one of the electrodes to which the IDS signal is applied includes one of the electrodes to which the pacing pulses are applied.

Further preferably, at least one of the pacing sites is in the left ventricle, and the IDS signal is applied to an electrode in the left ventricle.

Preferably, the control unit applies the IDS signal between during a time period which begins between about 0 and 100 ms after the onset of a pacing pulse applied by the control unit, wherein the time period is set so as to substantially eliminate the possibility that a propagating action potential will be generated responsive to application of the IDS signal. Preferably, the time period begins between about 10 and 50 ms after the onset of the pacing pulse.

Preferably, the IDS signal is applied in order to increase contractility of the heart or, alternatively or additionally, in order to increase systolic pressure generated by the heart.

In a preferred embodiment, the apparatus includes a sensor, which senses a physiological variable, wherein the control unit receives an input from the sensor and applies the IDS signal responsive thereto. Preferably, the sensor detects an electrical depolarization wave in the tissue. Alternatively (or additionally, the sensor senses a hemodynamic: parameter or senses motion. Preferably, the control unit controls application of the pacing pulses responsive to the variable. Further preferably the control unit makes a transition from a first stimulation mode to a second stimulation mode responsive to the variable.

BRIEF DESCRIPTION OF THE DRAWINGS

The present invention will be more fully understood form the following detailed description of the preferred embodiments thereof, taken together with the drawings, in which:

FIG. 1A is a graph of shortening vs. time, before, during, and after an IDS signal;

FIG. 1B is a graph of calcium concentration vs. time;

FIG. 2A is a graph of calcium concentration vs. time;

FIG. 2B is a graph of shortening vs. time;

FIG. 3 depicts two graphs vs. time, graph (a) representing concentration form vs. time, and graph (b) represents action potential vs. time; and FIG. 4 depicts two graphs of concentration force vs. time, (a) being a control and (b) representing the use of a drug.

DETAILED DESCRIPTION OF PREFERRED EMBODIMENTS

This invention is designed to modulate intracellular calcium concentration in a biological tissue using a non-excitatory electrical signal (IDS). In particular, the invention relates to the modulation of the intracellular calcium in cardiac muscle cells and thus the modulation of cardiac contractility. According to this invention a non-excitatory electrical field, current or voltage is passed through the tissue or in its proximity, resulting in either changing trans-membranal calcium ion fluxes or an intracellular calcium stores content. In another aspect of the invention the electrical field may interfere/enhance the affinity of intracellular calcium binding elements to calcium. In a further aspect the rise in intracellular calcium concentrations may initiate a cascade of events including, but not limited to, phosphorylation/dephosphorylation, gene transcription, and/or post translation modification.

Systems are disclosed which utilize the application of electrical current to a tissue, effecting tissue contractility by means of modulating intracellular calcium. At least one pair of electrodes is used for applying the signal. Electrode placement is adapted for achieving the maximum desired effect. The electrodes are attached to an either implantable or external device with programming capabilities. This device can be tested and calibrated non-invasively by external mechanisms. In addition, stimulation parameters can be adjusted by a similar programming mechanism.

The characteristics of the electrodes used for the stimulation are important. This invention utilizes both uni-polar and bi-polar electrode configurations.

A novel aspect of this method of modulating intracellular calcium in cells is the ability to adjust the timing and the amount of calcium increase/decrease using temporal electrical current rather than systemic pharmacological agents.

The accompanying figures show changes in intracellular calcium resulting from the application of the IDS signal together with experimental evidence on the effect of the IDS signal on the calcium handling in the cell. FIG. 1A represents the shortening of a single isolated myocyte measured using optical means. Each of the lines represents a single contraction of the myocyte. When the IDS signal was delivered, a marked increase in the myocyte shortening of 30.9±5% (n=10) was observed. The shortening returned to baseline when signal delivery was stopped.

FIG. 1B shows the optical measurements of calcium concentration from a single myocyte without the application of the IDS signal (dark line) and on top of it superimposed the intracellular calcium concentration during the delivery of the IDS signal (gray line). An increase of 26.6% (n=3) in the peak calcium level was observed. The calcium concentration changes were measured using the florescence ration of a calcium sensitive dye Fura-2 at two wavelengths, 340 nm and 380 nm. The same result showing a large increase in calcium concentration was measured from an isolated ferret heart using a Langendorf setting. The ventricle contraction force and contractility increased by up to 50%, and at the same time cellular calcium concentration, measured using Aquarine calcium sensitive dye, was increased by up to 50%.

FIGS. 2A and 2B show the effect of the IDS signal on the shortening and intracellular calcium of myocytes isolated from canine heart with heart failure (generated by repeated ischemia events). Each line represents an average of 20 consecutive beats before (black line) and during (gray line) the application of the signal. FIG. 2A shows an increase of 24.9±3.9% (n=11) in shortening. FIG. 2B shows an increase of 29.7% (n=3) in intracellular calcium measured using Fluo-3 fluorescence.

FIG. 3 depicts initial changes in contraction force and in action potential duration, measured using an intracellular electrode, during the first three beats of IDS signal application to a rabbit papillary muscle. The action potential duration when the IDS signal is applied (gray line in the lower trace) is superimposed on a control contraction (black line in the middle trace). Black lines, in the upper trace, mark the start of application of the IDS signal. The action potential duration immediately changes upon the application of the IDS signal from the first pulse. There is no significant difference between action potential duration in the consecutive beats. The contraction force behaves differently; there is a small increase in the contraction force on the first beat followed by a larger increase in the second beat and gradual changes until a plateau is reached after 5 to 6 beats. The underlying mechanism is that the IDS signal prolongs action potential duration. As a result of action potential prolongation the flow of calcium into the cell increases and generates two effects:

(1) immediate increase in the Sarcolemal calcium level causing the initial increase in the contraction force on the first beat; and (2) increase in the stored calcium in the Sarcoplasmatic Reticulum (SR) that is released during the following contractions and induces a larger increase in contraction until a new steady state is reached with higher contraction force.

The initial increase in the contractile force also supports the possible increase in the affinity of intracellular calcium binding elements that cause part of the increase in the contraction force.

FIG. 4 provides additional evidence supporting the hypothesis of calcium entry. The lower trace shows the increase in contraction force of a rabbit papillary muscle as a result of an IDS signal (shown as a black line on the upper trace). The initial increase in contraction on the first beat followed by the gradual change in the following beats is clearly seen. The middle trace shows the change in contraction force of the same muscle after the addition of the Ryanodine to the bath solution. Ryanodine prevents the accumulation of calcium in the Sarcoplasmatic Reticulum and therefore decreases the baseline contraction force. Upon the application of the IDS signal the contraction force increases immediately on the first beat, but no increase occurs during the following beats since the SR mechanism is disabled by the Ryanodine and no accumulation of calcium in the SR can contribute to the additional increase in contraction force exist.

All such variations, applications and subcombinations of elements are considered to be within scope of the present invention. It will thus be appreciated that the preferred embodiments described above are cited by way of example, and the full scope of the invention is limited only by the claims.

We claim:

1. A method of intentionally modulating the intracellular calcium properties in cardiac tissue, comprising:
   (a) applying a stimulation probe to cardiac tissue in a subject's body;
   (b) selecting a desired effect on intracellular calcium properties in said cardiac tissue;
   (c) providing pulse parameters of non-excitatory stimulation designed to achieve said desired effect on said intracellular calcium properties;
   (d) using said parameters to generate an electrical signal comprising said non-excitatory stimulation; and
   (e) conveying said electrical signal to the stimulation probe during a refractory period for the tissue, thereby applying said non-excitatory stimulation to said cardiac tissue.

2. The method of claim 1, wherein the stimulation probe comprises one or more stimulation probes.

3. The method of claim 1, wherein the desired effect comprises increasing the intracellular calcium concentration.

4. The method of claim 1, wherein said desired effect comprises decreasing the intracellular calcium concentration.

5. The method of claim 1, wherein the desired effect is an increase in intracellular calcium ion flux.

6. The method of claim 1, wherein the desired effect includes a return to a base line value for the intracellular calcium property.

7. The method of claim 1, wherein the desired effect includes a return to a base line level of the intracellular calcium property between heart beats.

8. The method of claim 1, wherein the parameters include applying said non-excitatory stimulation beginning between 0 and 100 milliseconds after local activation.

9. The method of claim 1, wherein said selecting comprises selecting a desired long term consequence.

10. The method of claim 9, wherein said long term consequence comprises gene transcription and/or post translation modification.

11. The method of claim 1, wherein said selecting a desired effect comprises selecting a transient effect.

12. The method of claim 1, wherein said desired effect is release or re-uptake of calcium from a sarcoplasmic reticulum.

13. A method of intentionally modulating intracellular calcium properties in cardiac tissue, comprising:
   (a) applying a stimulation probe comprising one or more stimulation electrodes to a subject's heart;
   (b) applying to said subject's body at least one sensor responsive to said subject's cardiac muscle activity;
   (c) receiving a sensing signal from said at least one sensor;
   (d) selecting a desired effect on intracellular calcium properties in said subject's heart;
   (e) determining parameters of a non-excitatory stimulation pulse for modulation of intercellular calcium concentration to achieve said desired effect, depending on said sending signal;
   (f) generating an electrical signal comprising said non-excitatory stimulation pulse responsive to said sensing signal; and
   (g) conveying said electrical signal to at least one of said one or more electrodes during a refractory period for the cardiac tissue thereby applying said non-excitatory stimulation pulse to said cardiac tissue.

14. The method of claim 13, wherein said desired effect comprises increasing the intracellular calcium concentration.

15. The method of claim 13, wherein said desired effect comprises decreasing the intracellular calcium concentration.

16. The method of claim 13, wherein the sensor is an electrode introduced into the heart, said sensor measuring said heart's electrical activity, and wherein generating the electrical signal comprises generating an electrical signal synchronized with said electrical activity sensed by said sensing electrode.

17. The method of claim 13, wherein the sensor is an external electrode attached to the subject's body surface, said electrode measuring an ECG signal, and wherein generating the electrical signal comprises generating an electrical signal synchronized with said ECG signal.

18. The method of claim 13, wherein at least one of the one or more of the stimulation electrodes also functions as a sensing electrode.

19. The method of claim 13, wherein generating the electrical signal comprises generating an electrical signal having a predetermined delay relative to the signal.

20. The method of claim 13, wherein applying the stimulation probe comprises applying a probe comprising a plurality of stimulation electrodes, and wherein generating and conveying the electrical signal comprises generating a sequence of electrical signals and applying each electrical signal in said sequence to a different one of said plurality of stimulation electrodes.

21. The method of claim 13, wherein generating and conveying the electrical signal comprises generating and conveying said electrical signal selectively, based on a characteristic of the signals received from the at least one sensor.

22. The method of claim 21, wherein generating and conveying the electrical signal comprises generating and applying said electrical signal at a rate dependent on the heart rate, but not equal to the heart rate.

23. The method of claim 21, wherein generating and conveying the electrical signal comprises detecting a cardiac arrhythmia and adjusting the application of said electrical signal responsive thereto.

24. The method of claim 21, wherein generating and conveying the electrical signal comprises detecting a QT interval in the signals received from the at least one sensor and generating pulses responsive thereto.

25. The method of claim 13, wherein generating the electrical signal comprises varying one or more parameters of the non-excitatory stimulation pulse, selected from the group consisting of the pulse voltage, current, duration, delay, and waveform frequency.

26. The method of claim 13, wherein the non-excitatory stimulation comprises a baseline pulse and a waveform of substantially higher frequency than the baseline pulse superimposed thereon.

27. The method of claim 26, wherein the waveform comprises a square wave.

28. The method of claim 13, further comprising, after step (g), another step (h) generating and conveying another electrical signal of opposite polarity thereto.

29. The method of claim 13, wherein applying the non-excitatory stimulation pulse comprises varying the extent of a portion of the area of the heart segment to which said stimulation pulse is applied.

30. The method of claim 29, wherein varying the extent comprises selectively addressing a net of stimulation electrodes implanted in the heart.

31. The method of claim 13, wherein applying the stimulation probe comprises inserting the one or more stimulation electrodes into multiple chambers of the heart.

32. The method of claim 13, wherein applying the stimulation probe comprises inserting at least one of the one or more stimulation electrodes into a blood vessel of the heart.

33. The method of claim 32, wherein inserting the at least one stimulation electrode comprises inserting the electrode into the coronary sinus.

34. The method of claim 13, wherein generating and conveying the electrical signal comprises generating and conveying electrical signals at selected times of the day.

35. The method of claim 13, wherein generating and conveying the electrical signal comprises generating and conveying electrical signals which increase the subject's cardiac output.

36. The method of claim 13, wherein generating and conveying the electrical signal comprises generating and conveying electrical signals which decrease the subject's cardiac output.

37. The method of claim 13, wherein generating and conveying the electrical signal comprises generating and conveying electrical signals which increase the efficiency of contraction of the heart.

38. The method of claim 1, wherein said desired effect comprises desired effects on calcium concentration and/or trans-membranal calcium ion flux and/or intracellular stores content.

39. The method of claim 38, wherein the property is ion flux.

40. The method of claim 38, wherein the property is intracellular stores content.

41. The method of claim 38, wherein the property is increased.

42. The method of claim 1 wherein the desired effect comprises increase of the property.

43. The method of claim 1 wherein the desired effect comprises decrease of the property.

44. The method of claim 1 wherein the pulse parameters comprise timing and/or voltage, current, duration, polarity, waveform, and frequency of the waveform of the stimulation.

45. The method of claim 1 wherein the parameters are selected for an individual subject.

46. The method of claim 13, wherein the properties include calcium concentration and/or trans-membranal calcium ion flux and/or intracellular stores content.

47. The method of claim 13, wherein the pulse parameters comprise timing and/or voltage, current, duration, polarity, waveform, and frequency of the waveform of the stimulation.

48. The method of claim 13, wherein said desired effect comprises an increase in intracellular calcium ion flux.

49. The method of claim 13, wherein the parameters include applying said non-excitatory stimulation beginning between 0 and 100 milliseconds after local activation.

50. The method of claim 13, wherein said selecting comprises selecting a long term consequence.

51. The method of claim 13, wherein said selecting a desired effect comprises selecting a transient effect.

52. The method of claim 13, wherein said desired effect is release or re-uptake of calcium from a sarcoplasmic reticulum.

53. A method for regulating the intracellular calcium properties in cardiac tissue, comprising:
   a. applying a stimulation probe to cardiac tissue in a subject's body;
   b. determining a desired intracellular calcium property of said tissue;
   c. generating an electrical signal comprising non-excitatory stimulation which has an effect on said intracellular calcium property commensurate with said desired regulation; and
   d. conveying said non-excitatory stimulation pulse to said cardiac tissue during a refractory period for said tissue.

54. The method of claim 53, wherein steps (c) and (d) are repeated as often as necessary to regulate the intracellular calcium properties in the cardiac tissue by the signal according to the desired regulation.

55. The method of claim 53, wherein the properties include calcium concentration and/or trans-membranal calcium ion flux and/or intracellular stores content.

56. The method of claim 53, wherein the desired regulation comprises increase of the property.

57. The method of claim 53, wherein the desired regulation comprises decrease of the property.

58. The method of claim 53, wherein modulating comprises increase of the property.

59. The method of claim 53, wherein modulating comprises decrease of the property.

60. The method of claim 53, wherein the desired calcium property comprises an increase in intracellular calcium ion flux.

61. The method of claim 53, wherein the conveying comprises applying said non-excitatory stimulation beginning between 0 and 100 milliseconds after local activation.

62. The method of claim 53, wherein said desired effect is release or re-uptake of calcium from a sarcoplasmic reticulum.

* * * * *